(12) United States Patent
Branch et al.

(10) Patent No.: US 11,737,711 B2
(45) Date of Patent: Aug. 29, 2023

(54) RESIDUAL JOINT DISPLACEMENT MONITORING AND COMPENSATION

(71) Applicant: RoboDiagnostics LLC, Atlanta, GA (US)

(72) Inventors: Thomas P. Branch, Atlanta, GA (US); Shaun K. Stinton, Chamblee, GA (US); Nathaniel K. DeJarnette, Lilburn, GA (US); Edward Dittmar, Marietta, GA (US); T. Christopher Madden, Atlanta, GA (US)

(73) Assignee: RoboDiagnostics LLC, Atlanta, GA (US)

( * ) Notice: Subject to any disclaimer, the term of this patent is extended or adjusted under 35 U.S.C. 154(b) by 397 days.

(21) Appl. No.: 16/685,705

(22) Filed: Nov. 15, 2019

(65) Prior Publication Data

US 2020/0155077 A1    May 21, 2020

Related U.S. Application Data

(60) Provisional application No. 62/768,310, filed on Nov. 16, 2018.

(51) Int. Cl.
*A61B 5/00* (2006.01)
*A61B 5/11* (2006.01)

(52) U.S. Cl.
CPC ............... *A61B 5/702* (2013.01); *A61B 5/11* (2013.01); *A61B 5/4585* (2013.01); *A61B 5/4884* (2013.01)

(58) Field of Classification Search
CPC ......... A61B 5/11; A61B 5/702; A61B 5/1121; A61B 5/4585; A61B 5/4884
See application file for complete search history.

(56) References Cited

U.S. PATENT DOCUMENTS

| | | | |
|---|---|---|---|
| 4,969,471 A | 11/1990 | Daniel et al. | |
| 5,348,025 A | 9/1994 | Wolfe | |
| 5,911,695 A | 6/1999 | Watkins et al. | |
| 5,935,086 A | 8/1999 | Beacon | |
| 2007/0055176 A1 | 3/2007 | Branch et al. | |
| 2009/0124936 A1 | 5/2009 | Branch et al. | |
| 2012/0046540 A1 | 2/2012 | Branch | |
| 2014/0081181 A1 | 3/2014 | Branch | |
| 2015/0032034 A1 | 1/2015 | Petrigliano et al. | |
| 2017/0143250 A1* | 5/2017 | Branch | A61B 5/4585 |
| 2017/0340278 A1* | 11/2017 | Imhauser | A61B 5/6835 |
| 2021/0251566 A1* | 8/2021 | Shultz | A61B 5/6828 |

* cited by examiner

*Primary Examiner* — Patrick Fernandes
*Assistant Examiner* — Anna Roberts
(74) *Attorney, Agent, or Firm* — Lempia Summerfield Katz LLC

(57) ABSTRACT

An apparatus for manipulation and evaluation of a joint includes a frame to support the joint and to facilitate an application of force away from the joint for the evaluation of the joint, a bracket assembly supported by, and moveable relative to, the frame, the bracket assembly being configured to engage the joint, and a sensor coupled to the bracket assembly such that the sensor is moved by displacement of the bracket assembly relative to the frame during the evaluation of the joint, the sensor being configured to generate a signal indicative of the displacement.

14 Claims, 13 Drawing Sheets

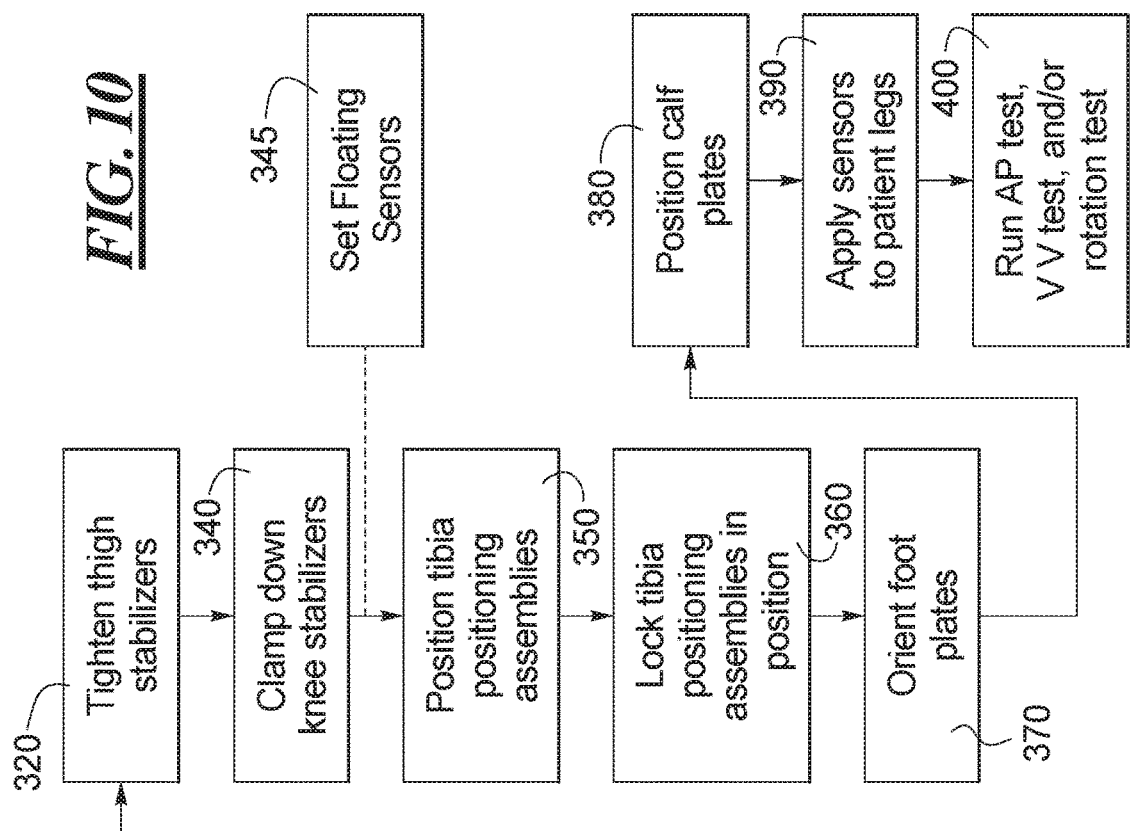
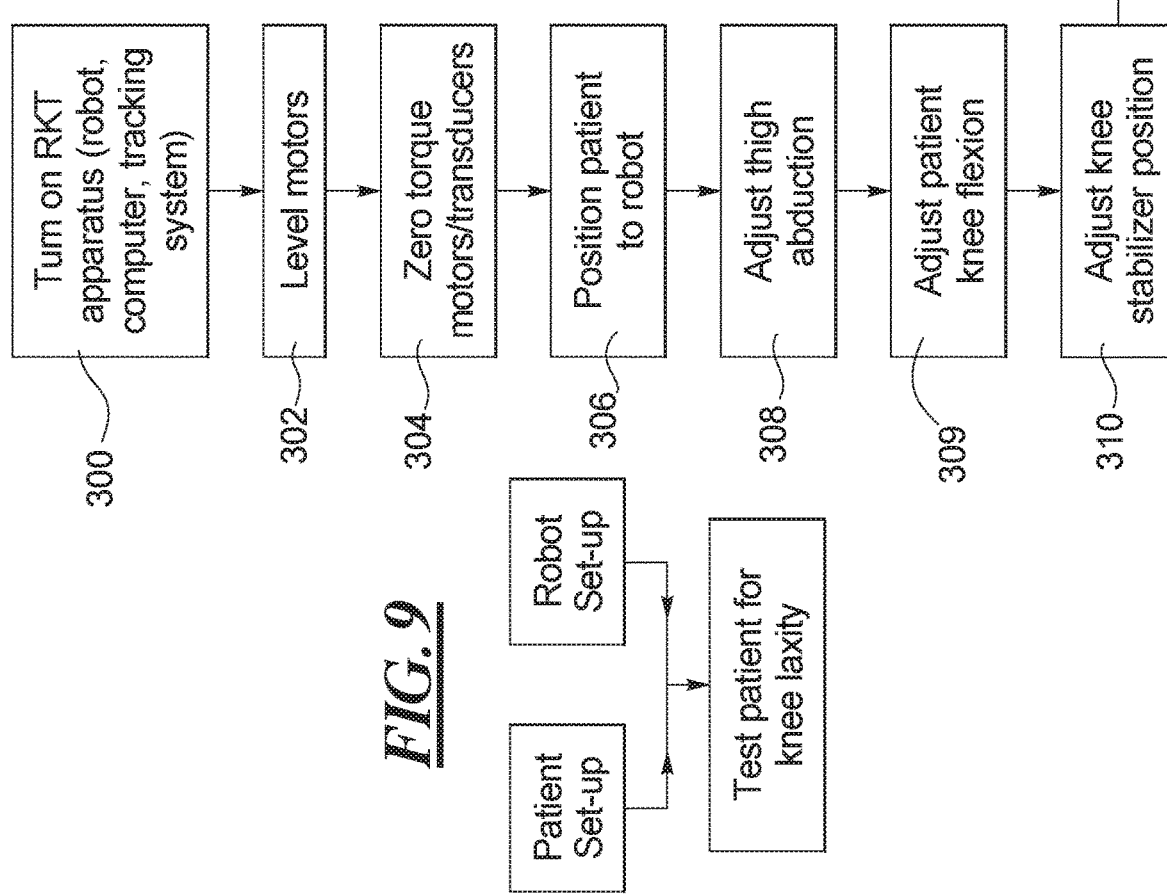

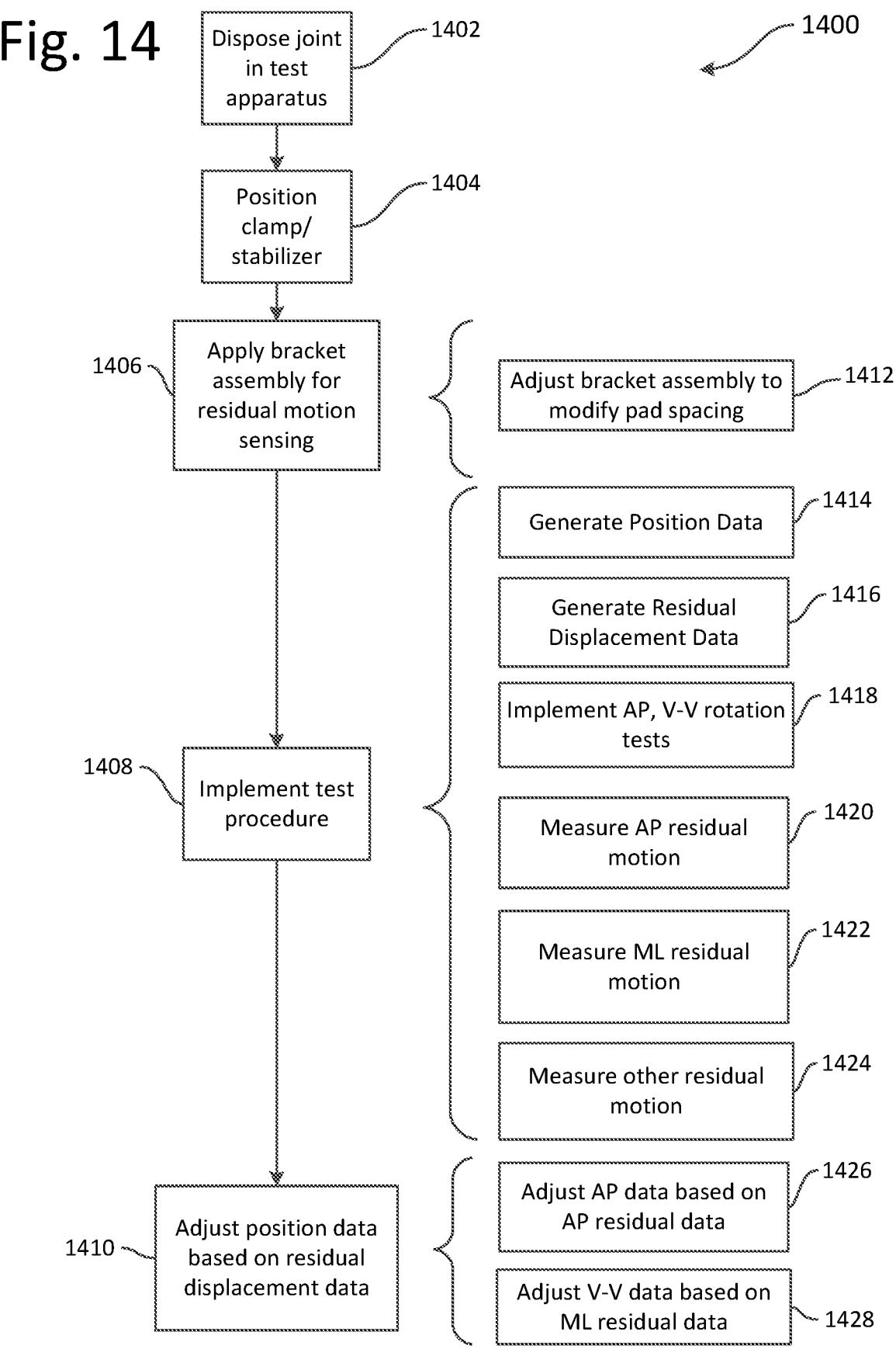

RESIDUAL JOINT DISPLACEMENT MONITORING AND COMPENSATION

CROSS-REFERENCE TO RELATED APPLICATION

This application claims the benefit of U.S. provisional application entitled "Residual Joint Displacement Monitoring and Compensation," filed Nov. 16, 2018, and assigned Ser. No. 62/768,310, the entire disclosure of which is hereby expressly incorporated by reference.

BACKGROUND OF THE DISCLOSURE

Field of the Disclosure

The disclosure relates to joint testing.

Brief Description of Related Technology

Knee injuries and ligament damage have been diagnosed using the Dial test (or internal-external rotation test), the Lachman test (or anterior-posterior drawer test), and the Varus-Valgus test. When performed manually by individual medical personnel, these tests are limited by the specific clinician's subjective evaluation. The subjective nature of the tests may hinder the precision or accuracy of the diagnosis.

Others have attempted to reduce the manual nature of such joint testing by applying an instrument to the knee joint during testing. Several devices have been developed in attempts to more accurately quantify the extent of injury or relative displacement and compliance of a ligament in the knee. For example, Medmetric Corp has developed the KT-1000 and KT-2000 devices for measurement of the anterior-posterior translation of the tibia with respect to the femur.

Joint testing in the past, both manual and instrumented, has been found to be inconsistent. For instance, inconsistencies arise both when testing the same patient from day to day and when two different examiners test the same patient. The inconsistencies arise in part from the accumulation of error introduced at different stages of an examination or diagnosis. Introducing significant error at any one or more steps during a test may greatly affect, and invariably reduce, the accuracy of the ultimate diagnosis. The degree of error may often overwhelm the ability to obtain an accurate diagnosis.

SUMMARY OF THE DISCLOSURE

In accordance with one aspect of the disclosure, an apparatus for manipulation and evaluation of a joint includes a frame to support the joint, a bracket assembly supported by, and moveable relative to, the frame, the bracket assembly being configured to engage the joint, and a sensor coupled to the bracket assembly such that the sensor is moved by displacement of the bracket assembly relative to the frame during the evaluation of the joint, the sensor being configured to generate a signal indicative of the displacement.

In accordance with another aspect of the disclosure, an apparatus for manipulation and evaluation of a joint of a subject includes a drive configured to apply force to the subject away from the joint to manipulate a first bone connected to the joint relative to a second bone connected to the joint, a frame that supports the drive, a clamp disposed between the frame and the subject to stabilize a part of the joint while the first bone is manipulated by the drive, a bracket assembly supported by, and slidable relative to, the frame, the bracket assembly including a pair of ends, each end of the pair of ends engaging a respective side of a pair of opposite sides of the joint, and a sensor coupled to the bracket assembly such that the sensor is displaced by translation of the bracket assembly relative to the frame, the sensor being configured to generate a signal indicative of the translation.

In accordance with yet another aspect of the disclosure, a method of manipulating and evaluating a joint includes disposing the joint in a joint test apparatus, positioning a clamp of the joint test apparatus to stabilize a part of the joint, applying a bracket assembly of the joint test apparatus to the part of the joint stabilized by the clamp, the bracket assembly being movable relative a frame of the joint test apparatus, generating, with a sensor coupled to the bracket assembly, data indicative of displacement of the bracket assembly relative to the frame during an evaluation of the joint by the joint test apparatus in which a second bone connected to the joint is manipulated, and adjusting position data for a bone manipulated by the joint test apparatus during the evaluation in accordance with the data indicative of the displacement to compensate for residual movement of the part of the joint stabilized by the clamp.

In connection with any one of the aforementioned aspects, the systems, devices, and/or methods described herein may alternatively or additionally include any combination of one or more of the following aspects or features. Respective ends of the bracket assembly engage medial and lateral sides of the joint. The displacement includes medial-lateral translation. The apparatus further includes a drive supported by the frame. The drive is configured to manipulate a bone connected to the joint in a first direction. The displacement is in a second direction different than the first direction. The apparatus further includes a clamp supported by the frame. The clamp is configured to stabilize a part of the joint during a joint evaluation in which a first bone connected to the joint is manipulated relative to a second bone connected to the joint. The displacement is indicative of residual movement of the stabilized part of the joint during the joint evaluation. The apparatus further includes a processor configured to adjust position data for the first bone in accordance with data indicative of the displacement to compensate for the residual movement of the stabilized part of the joint during the joint evaluation. The apparatus further includes a linear bearing mounted on the frame. The bracket assembly includes a bar disposed in the linear bearing. The sensor is mounted on the bar such that the displacement includes translation of the bar within the linear bearing. The apparatus of claim 7, further including a rod attached to the sensor. The rod extends from the sensor to establish a contact point with the joint. The sensor is slidably coupled to the bar to allow displacement of the rod and the sensor as a result of movement of the joint in a direction other than a direction of the translation. The bracket assembly includes a pair of link posts extending from the bar to position respective ends of the bracket assembly along opposite sides of the joint, a pair of arms, each arm of the pair of arms extending laterally inward from a respective link post of the pair of link posts toward a respective side of the opposite sides of the joint, and a pair of pads, each pad of the pair of pads disposed on a respective side of the opposite sides of the joint. Connections between the pair of arms and the pair of link posts are adjustable to modify a spacing between the pair of pads. The drive is configured to manipulate a bone connected to the joint in a first direction. The translation is in a second direction different than the first direction. The translation is indicative of residual movement of the joint during the joint evaluation remaining after stabilization by the clamp. The apparatus further includes a rod attached to the sensor. The rod extends from the sensor to establish a contact point with the joint. The sensor is slidably coupled to the bracket assembly to allow displacement of the rod and the sensor as a result of movement of the joint in a direction other than a direction of the translation. The bracket assembly includes a bar slidably engaged with the frame, a pair of link posts extending from the bar to position respective ends of the bracket assembly along the opposite sides of the joint, a pair of arms, each arm of the pair of arms extending laterally inward from a respective link post of the pair of link posts toward a respective side of the opposite sides of the joint, and a pair of pads, each pad of the pair of pads disposed on a respective side of the opposite sides of the joint. The evaluation includes internal-external rotation of the joint. The displacement is medial-lateral translation of the joint. The evaluation includes a varus-valgus test of the joint. The displacement is medial-lateral translation of the joint. The method further includes measuring movement of the joint in a direction other than a direction of the displacement via a rod that extends from the sensor to establish a contact point with the joint. Applying the bracket assembly includes adjusting the bracket assembly to modify a spacing between a pair of pads of the bracket assembly.

BRIEF DESCRIPTION OF THE DRAWING FIGURES

For a more complete understanding of the disclosure, reference should be made to the following detailed description and accompanying drawing figures, in which like reference numerals identify like elements in the figures.

FIG. 9 is a flow diagram of a method of manipulating and evaluating a knee in accordance with one example.

FIG. 10 is a flow diagram depicting the method of FIG. 9 in greater detail.

FIG. 14 is a flow diagram of a method of manipulating and evaluating a joint in which data is adjusted to compensate for residual movement of a stabilized part of a joint in accordance with one example.

Figure 1:
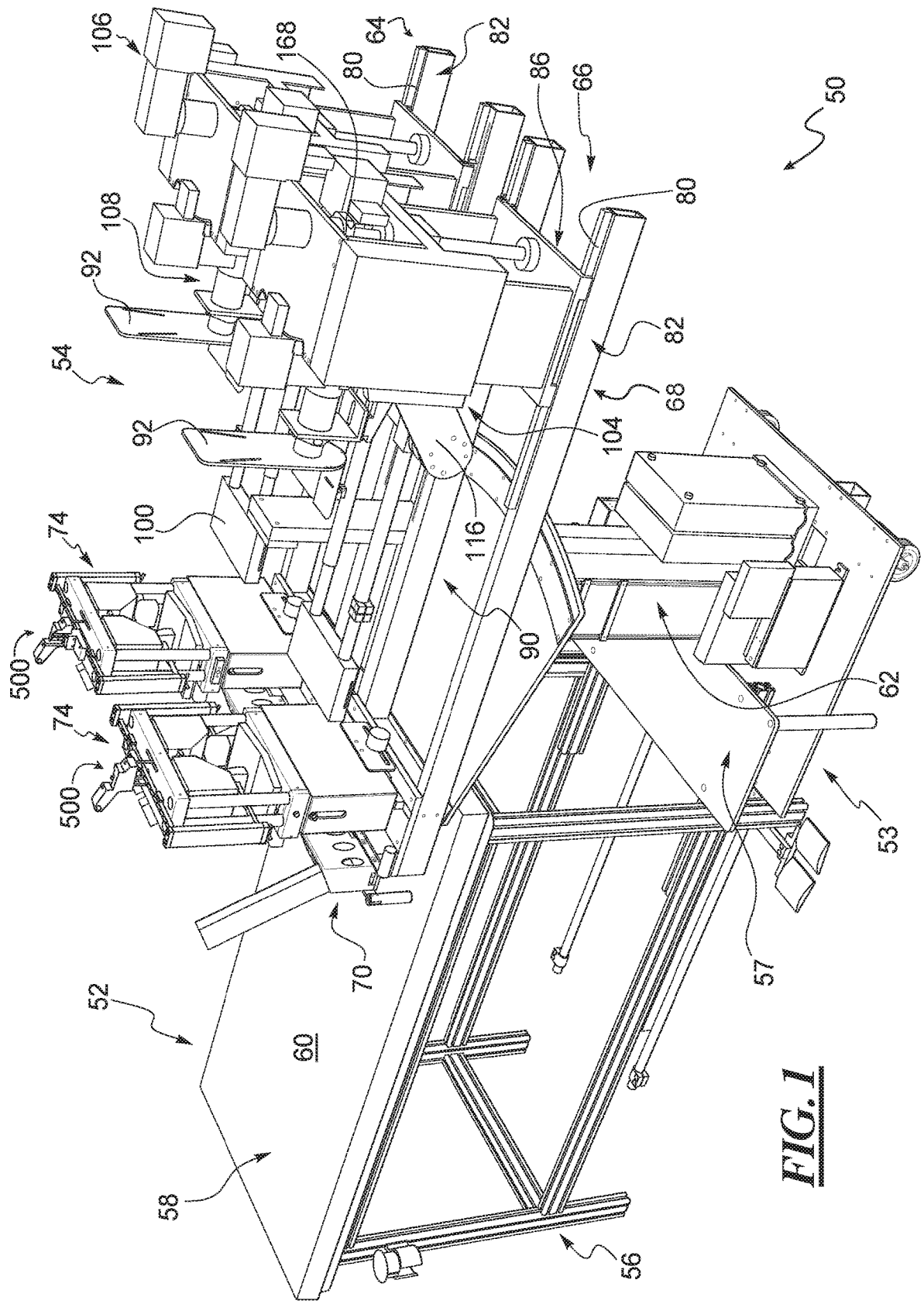
FIG. 1 shows a perspective view of a robotic knee testing (RKT) apparatus in accordance with one example.

The embodiments of the disclosed apparatus, devices, and methods may assume various forms. Specific embodiments are illustrated in the drawing and hereafter described with the understanding that the disclosure is intended to be illustrative. The disclosure is not intended to limit the invention to the specific embodiments described and illustrated herein.

DETAILED DESCRIPTION OF THE DISCLOSURE

Systems and methods for residual joint movement monitoring and compensation are described. The systems and methods are useful in connection with joint testing and evaluation procedures in which a joint is stabilized. For instance, one part of the joint (e.g., a femur of a knee joint) is stabilized while a test apparatus applies a force (directly or indirectly) to another part of the joint (e.g., a tibia of the knee joint). Measurement data indicative of the movement resulting from the force is collected by the test apparatus. The measurement data is then corrected to compensate for any residual motion of the stabilized part of the joint. The correction allows the joint testing to not assume that the stabilized part(s) of the joint remain entirely fixed.

In some knee joint testing examples, a knee testing system includes a knee clamping assembly that attempts to isolate motion in the knee by locking the femur in place. The knee clamping assembly does not prevent all motion of the femur. For instance, during a varus-valgus test, the femur still exhibits anterior-posterior translation and medial and lateral translation. Such residual motion may result from the limitations of pads used to position and stabilize the knee in the knee testing system. For example, a pad on the posterior side of the knee does not touch the condyles of the femur. Instead, the pad stops farther up the rounder shaft of the femur. Two pads used to lock the patella of the knee into the trochlea are angled in a way to center the knee in the test apparatus and lock down the patella. But such angled trapping of the anterior portion of the knee may still allow the knee to translate medially and laterally. Medial-lateral displacement may arise from pivoting around the pads during valgus/varus and rotation testing. The medial-lateral displacement may alternatively or additionally arise from limitations on the extent to which a body segment can be clamped without causing pain for the patient. The disclosed systems and methods allow and monitor such movement rather than try to limit or eliminate the movement entirely with, for instance, rigid pads.

The monitoring of residual movement of the joint facilitates an accurate assessment of the laxity of the joint in multiple ways. Unlike other laxity testing techniques, the disclosed systems and methods do not apply force to the joint (e.g., at the joint) in the degree of freedom being monitored. For instance, other knee testing techniques might apply force to the medial and lateral side of the knee to evaluate joint laxity (e.g., varus-valgus laxity). As described herein, the disclosed systems and methods may instead stabilize a part of the joint (e.g., the femur), apply force away from the joint (e.g., at the foot), and then measure both the resulting motion of the unstabilized part of the joint (e.g., the tibia) and the resulting residual motion of the stabilized part of the joint. The data measured for the unstabilized part of the joint (e.g., the tibia) may then be corrected to compensate for the residual motion. In this way, the correction provides a more accurate measurement of tibial motion relative to the femur.

The disclosed systems and methods may be configured to implement corrections in one or more degrees of freedom and/or in connection with one or more joint tests. For example, the residual motion may include displacement (e.g., translation) in the medial-lateral direction, the anterior-posterior direction, and/or the axial direction. The residual motion may be monitored during varus-valgus testing, internal-external rotation testing, and/or other tests. The residual motion may alternatively or additionally involve rotational motion.

The monitoring of the medial-lateral or other residual motion may utilize a bearing arrangement. For example, in some cases, a linear bearing is used to trap or restrict movement in other directions, while still allowing the stabilized part of the joint to move in a direction of residual motion of interest. A sensor secured to a rail or other structure guided by the bearing(s) is thus floating or otherwise free to move in the residual motion direction(s). The disclosed systems and methods may use one or more pads (e.g., medial and lateral pads) to establish initial conditions for the sensor. The adjustments may allow for a difference in joint part size (e.g., femur size).

In some cases, the apparatus used to monitor residual motion in multiple directions may share one or more components. For instance, the disclosed systems may be configured such that a single sensor is used to monitor residual motion in both the medial-lateral and anterior-posterior directions. The medial-lateral residual motion and the anterior-posterior residual motion may thus be concurrently monitored. Notwithstanding the foregoing, one or more additional sensors may be used to measure residual motion in a rotational or other degree of freedom. Examples of residual rotational measurement sensor arrangements are described in U.S. Patent Publication No. 2017/0143250 ("Floating Patella Sensor, Knee Stabilizer with Same and Robotic Knee Testing Apparatus with Same"), the disclosure of which is hereby incorporated by reference. As another example, an additional slide or other sensor arrangement may be added to measure residual motion in the axial direction.

Although described below in connection with knee testing, the disclosed systems and methods are well suited for use in evaluating a variety of other joints. For example, the disclosed systems and methods may be used to evaluate joints, such as elbow joints, shoulders, ankles, wrists, and the like. The RKT apparatus and other devices described herein may thus alternatively be configured to manipulate and evaluate a wide range of other joints.

The disclosed systems and methods use a joint testing apparatus, such as an RKT apparatus, to provide a controlled application of torque during joint examination. The apparatus may control the magnitude, direction, and rate of torque application for one or more tests. Both the apparatus and the tests may vary from the examples described herein. The monitoring of the residual displacement of a stabilized part of the joint may vary accordingly.

Turning now to the drawings, FIG. 1 shows an RKT apparatus 50 configured for manipulation and evaluation of a knee joint in accordance with one example. Various features, components, or other aspects of the apparatus 50 may be configured as described in U.S. Patent Publications Nos. 2014/0081181 and 2012/0046540, the entire contents of which are hereby incorporated herein by reference.

Figure 2:
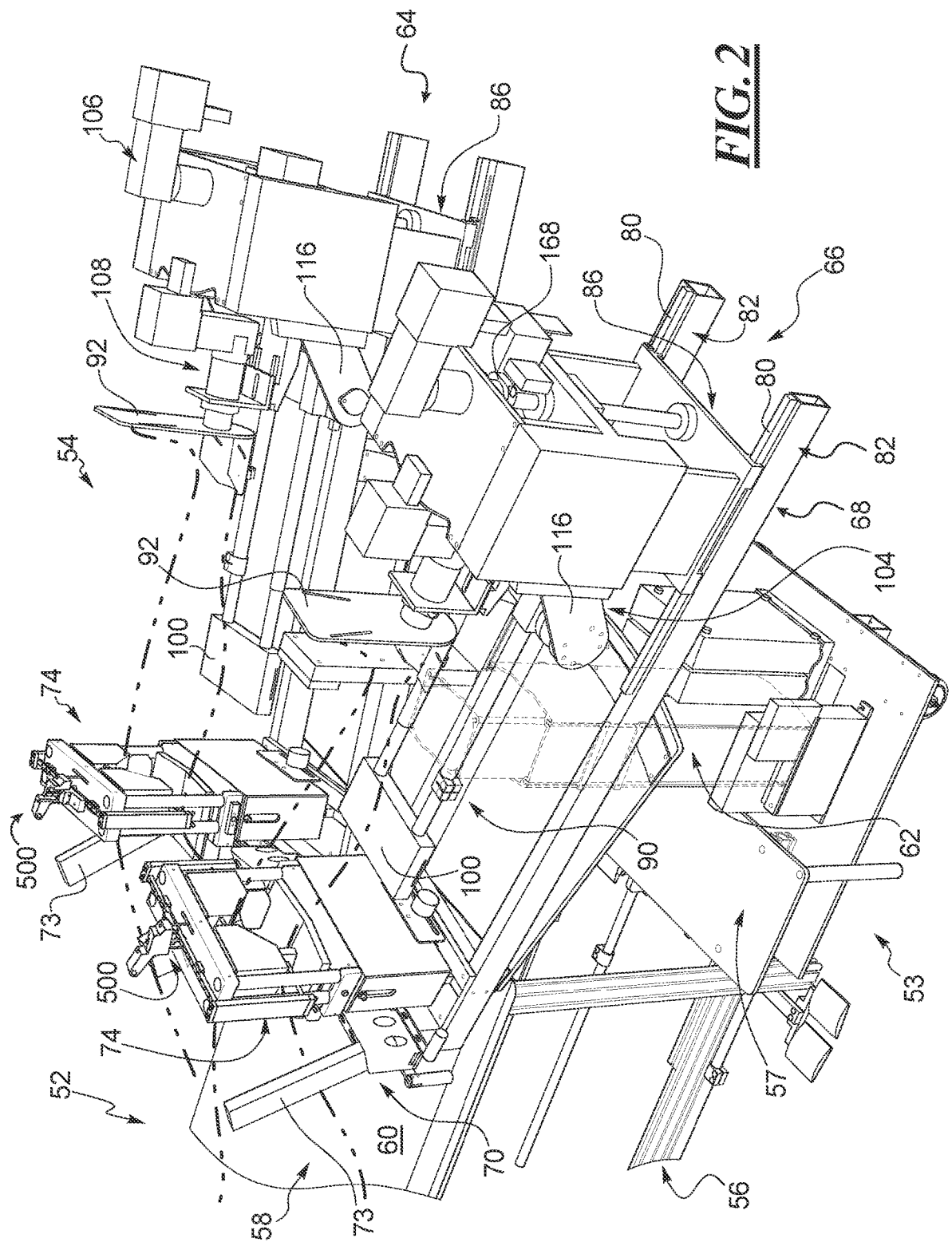
FIG. 2 shows an enlarged view of a joint manipulation mechanism or robot of the robotic knee testing apparatus of FIG. 1, the enlarged view depicting left and right legs of a patient positioned relative to left and right leg portions of the robot.

The RKT apparatus 50 of FIG. 1 has a patient support, i.e., a table assembly 52. The RKT apparatus 50 also has a robotic device or limb or joint manipulation mechanism, identified for ease of description herein as a robot 54, positioned at one end or edge of the table assembly 52. The robot 54 is supported by a robot positioning system 53. The robot positioning system 53 is configured so that the robot 54 is movable relative to the table assembly 52. The table assembly 52 in this example has a supporting frame that is identified herein as a base 56 beneath a patient platform 58. The base 56 is configured to rest on a floor or surface and to support the patient platform 58 above the floor. The patient platform 58 may include a substantially rigid or sturdy panel (not shown) capable of holding and supporting a patient thereon. The panel may be affixed to or otherwise supported by the base 56. The panel of the patient platform 58 may underlie a padded surface 60, which may include a textile or fabric material that covers a cushion, padding, or the like (also not shown). As shown in FIGS. 1 and 2, the patient support may include a step 57 positioned at the distal end of the table assembly 52 to assist a patient to step up onto the patient platform 58.

The configuration and construction of the table assembly 52, robot positioning system 53, and step 57 may vary considerably from the example shown. For instance, the robot positing system 53, base 56, the patient platform 58, and step 57 may each be altered in configuration, size, shape, orientation, height, construction, materials, and the like. The patient support need not be a table, but instead may be a chair, a suspension system, or other suitable structure that is capable of properly positioning and retaining a patient relative to the robot 54 for testing and examination or evaluation. The table assembly 52, robot positioning system 53, and/or step 57 may further include additional features that may be used to assist in the patient sitting on the patient platform, to assist in positioning a patient on the patient platform, to assist in maintaining a patient's position on the platform, or to otherwise enhance patient comfort or improve performance of the table assembly, the RKT apparatus, or both.

The positioning system 53 of the RKT apparatus 50 may be configured to allow movement of the robot 54 relative to the table assembly 52. The positioning system 53 is adjustably connected to the table assembly 52 in this example. The positioning system 53 has a column lift 62 that may raise and lower the robot 54 as well. In this example, the positioning system 53 may be configured to further assist a patient in getting onto the patient platform 58, as well as to aid in positioning the patient for testing.

Figure 3:
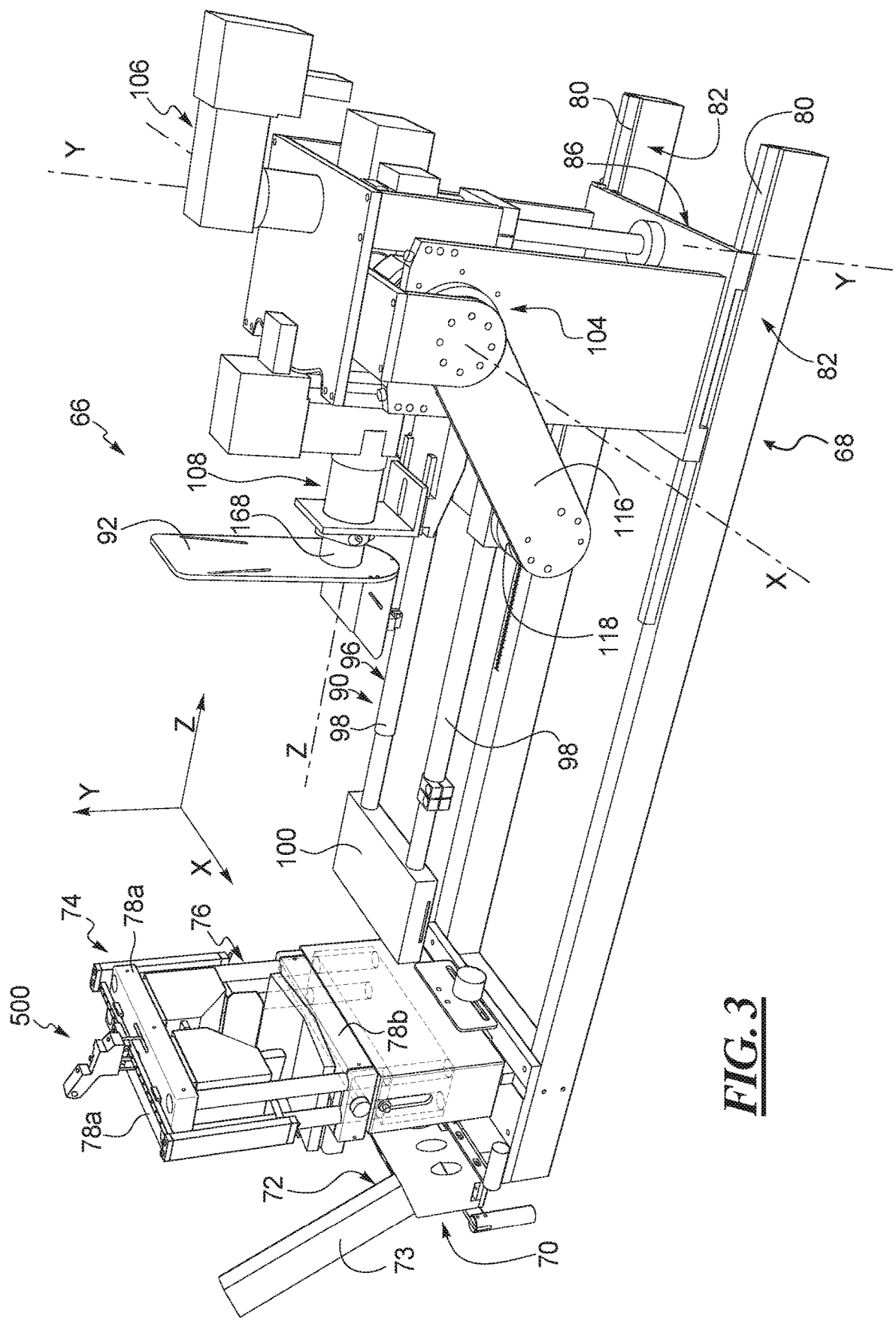
FIG. 3 shows a right leg portion of the robot of FIG. 2 and depicts an X-Y-Z coordinate system defined by the right leg portion.

In this case, as shown in FIGS. 2 and 3, the robot 54 has a left leg testing and evaluation mechanism and a right leg testing and evaluation mechanism, each mechanism respectively identified herein as a left leg portion 64 and a right leg portion 66 of the robot. The left and right leg portions 64, 66 have substantially the same construction, and may be essentially identical. Each portion is also constructed to support and evaluate a left leg and right leg, respectively, of a patient. Like reference numerals are accordingly used herein to identify common parts of each of the two leg portions 64, 66 that have the same construction.

Each of the left and right leg portions 64, 66 has a sub-frame 68 that, in this example, is supported directly or indirectly by the robot positioning system 53. Each sub-frame 68 supports the components and parts of the corresponding left and right leg portions 64, 66. For ease of description, the right leg portion 66 of the robot 54 is described in some detail below with the understanding that the left leg portion 64 has or may have the same overall construction. In other cases, the RKT apparatus 50 may have only one leg portion for evaluating only one leg of a patient at a time.

Figure 4:
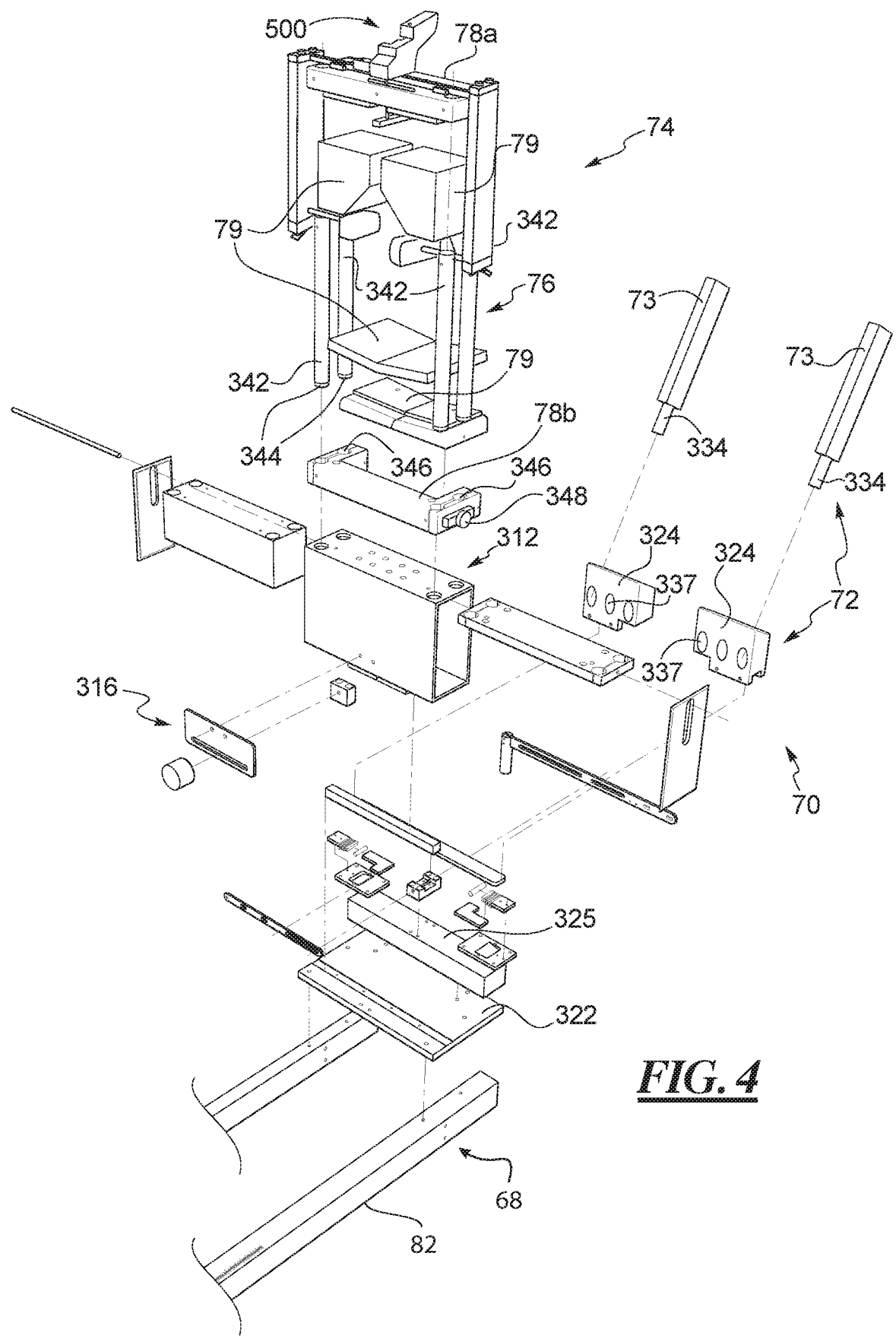
FIG. 4 shows an exploded view of a thigh immobilizer and a knee stabilizer of the right leg portion of FIG. 3.
Figure 5:
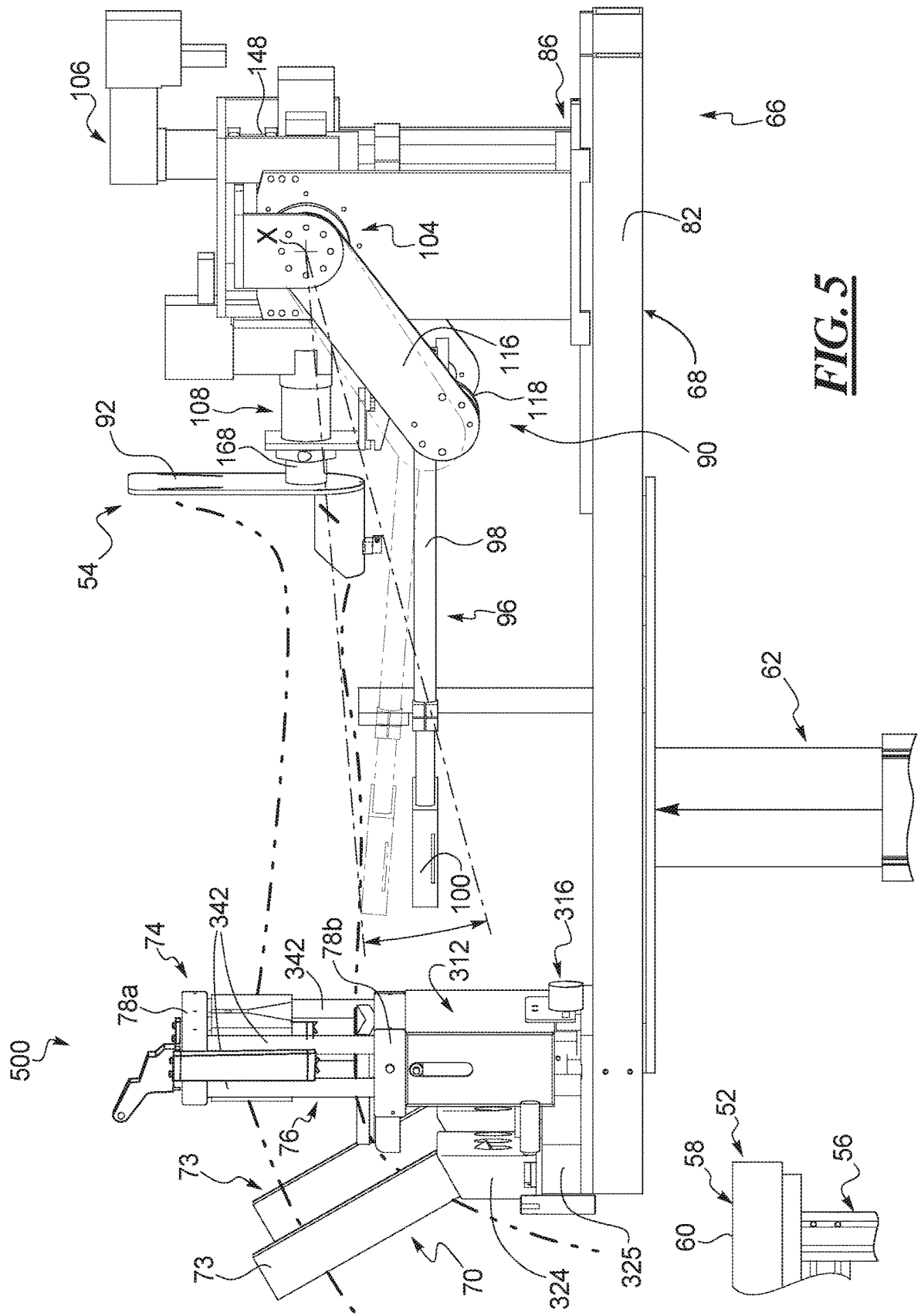
FIG. 5 shows a side view of the robot of FIG. 2 as viewed from the right leg portion side of the robot and illustrates anterior-posterior motion about the X-axis of a tibia positioning assembly of the right leg portion.

As depicted in FIGS. 3-5, the right leg portion 66 has a thigh clamp or immobilizer 70 positioned closest to the table assembly 52. The thigh immobilizer 70 may be mounted to the robot positioning system 53 or the sub-frame 68, or may be otherwise mounted to a portion of the RKT apparatus 50 in a manner suitable for use as described below. The thigh immobilizer 70 may be constructed to be adjustable in clamping width and in lateral position to accommodate a wide range of patients of different size and body type. The thigh immobilizer 70 may be positioned or capable of being positioned to contact a portion of a patient's upper leg or thigh above the knee.

The thigh immobilizer 70 in this example has a pair of femur clamping elements 72. In this case, the femur clamping elements 72 are configured as medial and lateral clamping elements that are laterally spaced apart and width-wise adjustable relative to one another. Though not shown herein, the clamping elements 72 may include a pad or pads on the thigh facing surfaces, if desired, to provide a degree of comfort for a patient. The femur clamping elements 72 may be side-to-side adjusted relative to one another in order to clamp or otherwise securely hold a patient's right femur and thigh in a substantially fixed side-to-side position during testing, evaluation, or treatment, as described below. The configuration and construction of the thigh immobilizer 70 may vary considerably from the example shown herein. The clamping elements 72 may be replaced by other suitable securing or clamping devices or elements and the mechanisms to adjust and secure the thigh. The thigh immobilizer 70 may thus vary accordingly.

In the example shown in FIGS. 3-5, the right leg portion 66 also has a knee stabilizer 74 positioned adjacent the thigh immobilizer 70. The knee stabilizer 74 may also be mounted to, or otherwise supported by, the robot positioning system 53 or the sub-frame 68, or may be otherwise mounted to or supported by a portion of the RKT apparatus 50 in a manner suitable for use as described below. The knee stabilizer 74 may be constructed to be adjustable in clamping height and in lateral position to accommodate a wide range of patients of different size and body type. The knee stabilizer 74 may be positioned or capable of being positioned to contact the knee or patella at the lower end of a patient's femur and thigh, as depicted in FIG. 5.

The knee stabilizer 74 acts as a patellar clamp or other knee stabilization mechanism. The knee stabilizer 74 may include a framework 76 arranged to surround and clamp onto a patient's joint or knee. The knee stabilizer 74 in this example has a pair of patellar clamping elements 78a, 78b that are vertically spaced apart and adjustable relative to one another along the framework 76. Each clamping element 78a, 78b may be or include a plate or bar that extends laterally across the knee. One or both of the patellar clamping elements 78a, 78b are vertically adjustable in order to clamp or otherwise securely hold the lower end of a patient's right femur and patella in a substantially fixed vertical position during testing, evaluation, or treatment, as described below. The knee stabilizer 74 may also be capable of being secured in a fixed selected lateral position, once properly adjusted for a given patient, relative to the table assembly 52 and/or robot 54 during testing. The configuration and/or construction of the knee stabilizer 74 may vary considerably from the example shown herein. The patellar clamping elements 78a, 78b may thus be replaced by other suitable securing or clamping devices or elements. Other aspects of the mechanisms to adjust and secure the knee stabilizer 74 may also vary.

The knee stabilizer 74 may include a plurality of substantially rigid and/or resilient pads 79 (FIG. 4). In this example, the knee stabilizer 74 includes upper and lower pads 79 on the patellar clamping elements 78a, 78b. The pads 79 may be configured and arranged to lie adjacent the patient's knee, preventing the framework 76 and the patellar clamping elements 78a, 78b, respectively, from directly contacting the patient's knee. The pads 79 may be solid, hollow, pressurized, hydraulically filled, pneumatically filled, or the like and may be rubber, foam, or otherwise formed of suitable materials. In one example, the pad or pads 79 on the upper patellar clamping element 78a may be wedge-shaped. Together, the pads 79 define a V-shaped opening within the framework 76. The patient's leg may then be captured within the V-shaped opening as the upper and lower patellar clamping elements 78a, 78b are drawn toward one another to capture and stabilize the patient's knee during a test procedure.

The thigh immobilizer 70 and/or the knee stabilizer 74 may be mechanically adjustable to manually fit and accommodate different sized patients. In one alternative, the thigh immobilizer 70 and/or the knee stabilizer 74 may be electrically operable to adjust the femur clamping elements 72, the patellar clamping elements 78a, 78b, respectively, or both. In another alternative example, the femur clamping elements 72 and/or the patellar clamping elements 78a, 78b may be pneumatically or hydraulically operable to adjust the thigh immobilizers 70 and knee stabilizers 74. In yet another alternative, the thigh immobilizer 70, the knee stabilizer 74, or both, may include two or more such systems or mechanisms for adjusting the respective clamping elements.

The thigh immobilizer 70 and/or femur clamping elements 72 and the knee stabilizer 74 and/or framework 76 and patellar clamping elements 78a, 78b may be formed of metal, plastic, or other suitable materials. The thigh and knee stabilizers 70 and 74 may vary in shape, configuration and construction, as desired. The thigh immobilizers 70 and knee stabilizers 74, in combination, are intended to secure a patient's leg to hold the femur and patella in a vertically (knee stabilizer) and laterally (thigh stabilizer) substantially fixed position during a test, evaluation, or treatment cycle. Features and aspects of the disclosed thigh immobilizers 70 and knee stabilizers 74 may vary considerably while accomplishing this objective.

In the example shown in FIGS. 3-5, the sub-frame 68 is configured to define or carry one or more slide tracks 80 carried on the free end of the sub-frame 68 that is distal or spaced from the table assembly 52. The sub-frame 68 is formed having a plurality of rails 82 that extend lengthwise. The tracks 80 may be formed as an integrated part of the rails 82 or other sub-frame components or may be separately mounted to or supported by the rails. One or more trucks or carriages, hereinafter a sled assembly 86, is mounted on or supported by the sub-frame 68 and is slidable along the tracks 80.

As depicted in FIGS. 2, 3, and 5, the right leg portion 66 further includes a tibia positioning assembly 90 that is mounted on the sub-frame 68. In this example, the tibia positioning assembly 90, or at least a portion of the assembly, is carried on the sled assembly 86. Thus, the tibia positioning assembly 90, or at least a portion thereof, is slidable lengthwise along the tracks 80 of the sub-frame 68 on the sled assembly 86, and thus is movable relative to the table assembly 52 and/or to the thigh immobilizers 70 and knee stabilizers 74.

In general, the tibia positioning assembly 90 has a foot holder. In this example, the foot holder includes a foot plate 92 that faces toward the thigh immobilizers 70 and knee stabilizers 74. The tibia positioning assembly 90 also has a tibia rod device 96 with one or more rods 98 and a calf plate 100 at or near a distal end of the tibia rod device. The one or more rods 98 may be lengthwise adjustable. In the example shown in FIGS. 3, 5, and 6, the tibia rod device 96 has two tibia rods 98, each of which has two telescoping and lockable segments that permit length adjustment of the rods 98. The telescoping segments permit adjustable positioning of the calf plate 100 relative to the foot plate 92 to accommodate different sized patients. During use, the calf plate 100 lies under and contacts a patient's calf below the knee and the foot plate 92 bears against the sole of the patient's foot. The foot plate 92 may be configured to physically constrain and hold the foot of a patient against the contact surface. In some cases, the foot plate 92 may employ one or more straps that secure the sole of their foot to the foot plate 92. Likewise, the calf plate 100 may be configured to physically constrain the patient's leg to the calf plate, e.g., for some tests, or may merely lie against and under the patient's calf while not being otherwise secured to the leg, e.g., for other tests.

With reference to FIGS. 3 and 5-7, the tibia positioning assembly 90 has a drive system with a number of drive components configured to impart specific and controllable movements to the lower leg of a patient. The drive system in this example has a first drive, i.e., an X-axis drive 104 as identified herein, which is oriented to define and provide rotation about a first axis, i.e., an X-axis as identified herein, which in this example lies generally laterally across the tibia positioning assembly 90. The drive system also has a second drive, i.e., a Y-axis drive 106 as identified herein, which is oriented to define and provide rotation about a second axis, i.e., a Y-axis as identified herein, which in this example lies generally vertically through the tibia positioning assembly 90, though not quite intersecting the X-axis, as described below. The drive system further has a third drive, i.e., a Z-axis drive 108 as identified herein, which is oriented to define and provide rotation about a third axis, i.e., a Z-axis as identified herein, which in this example lies lengthwise along the tibia positioning assembly 90. The three axes define a coordinate system and this coordinate system is identified as an X-Y-Z coordinate system for the right leg portion 66 of the robot 54 in this example. The robot 54 will also have a similar X-Y-Z coordinate system specific to the left leg portion 64, but independent of the coordinate system for the right leg portion 66.

In the example shown, the RKT apparatus is configured to implement tests involving anterior-posterior motion, Varus-valgus motion, and tibial rotation. In other cases, the RKT apparatus may be configured to test only one or two of anterior-posterior motion, Varus-valgus motion, or tibial rotation, instead of all three tests. In such cases, the drive system may include only one or two of the X-axis, Y-axis, or Z-axis drives instead of all three drives. The methods and procedures described herein may be modified to accommodate such robots that have fewer than all three drives. In still other cases, the X-Y-Z axes of the aforementioned coordinate systems may all intersect with one another and may all be orthogonal to one another. In still other examples, none or only two of the axes may intersect and/or none or only two of the axes may be orthogonal to one another.

The X-axis drive 104 may include a first motor, such as an electric motor, a gearbox, and an output shaft that is driven by the motor and gearbox. Opposite ends of the output shaft in this example are fixedly coupled to the upper ends of respective drive links 116 on opposite sides of a housing that encloses the motor, gearbox, and shaft. The lower end of one of the drive links 116 is coupled or fixed to an X-axis torque transducer 118. The torque transducer 118 is also coupled or fixed to an element coupled to fixed segments of the tibia rods 98, as shown in FIGS. 3 and 5.

With reference to FIG. 5, the X-axis drive 104 is configured to conduct an anterior-posterior or A-P test on a patient's knee. Position sensors may be applied to appropriate locations on the right leg of the patient. The X-axis drive 104 imparts force about the X-axis to initiate anterior-posterior motion in the tibia part of the knee joint relative to the fixed femur part of the knee joint of the patient, as shown in FIG. 5. The motor may reversibly rotate the output shaft through an arc about the X-axis whereby the upper ends of the drive links 116 are rotated through the same arc. This in turn moves, i.e., raises or lowers the lower ends of the drive links 116, which in turn raises or lowers the tibia rods 98. Movement of the tibia rods 98 raises or lowers the calf plate 100 carried on the tibia rods. The X-axis torque transducer 118 measures the applied torque caused by the load applied at the calf plate 100 as the calf plate pushes up on the patient's tibia or the tibia rods 98 pull down on the patient's tibia. Motion (or position) and load data may be collected by a processor from the sensors relative to the motion in the patient's leg and from the X-axis torque transducer 118 relative to the torque or applied force.

The above-described anterior-posterior movement components of the tibia positioning assembly 90 may vary considerably from the example shown and described herein. Likewise, the configuration and construction of the drive links 116, tibia rods 98, and calf plate 100 may also be varied. The mechanisms or devices that are used to secure a patient's leg to the tibia rods 98 and to the foot plate 92, if and when needed for testing, may also vary.

Figure 6:
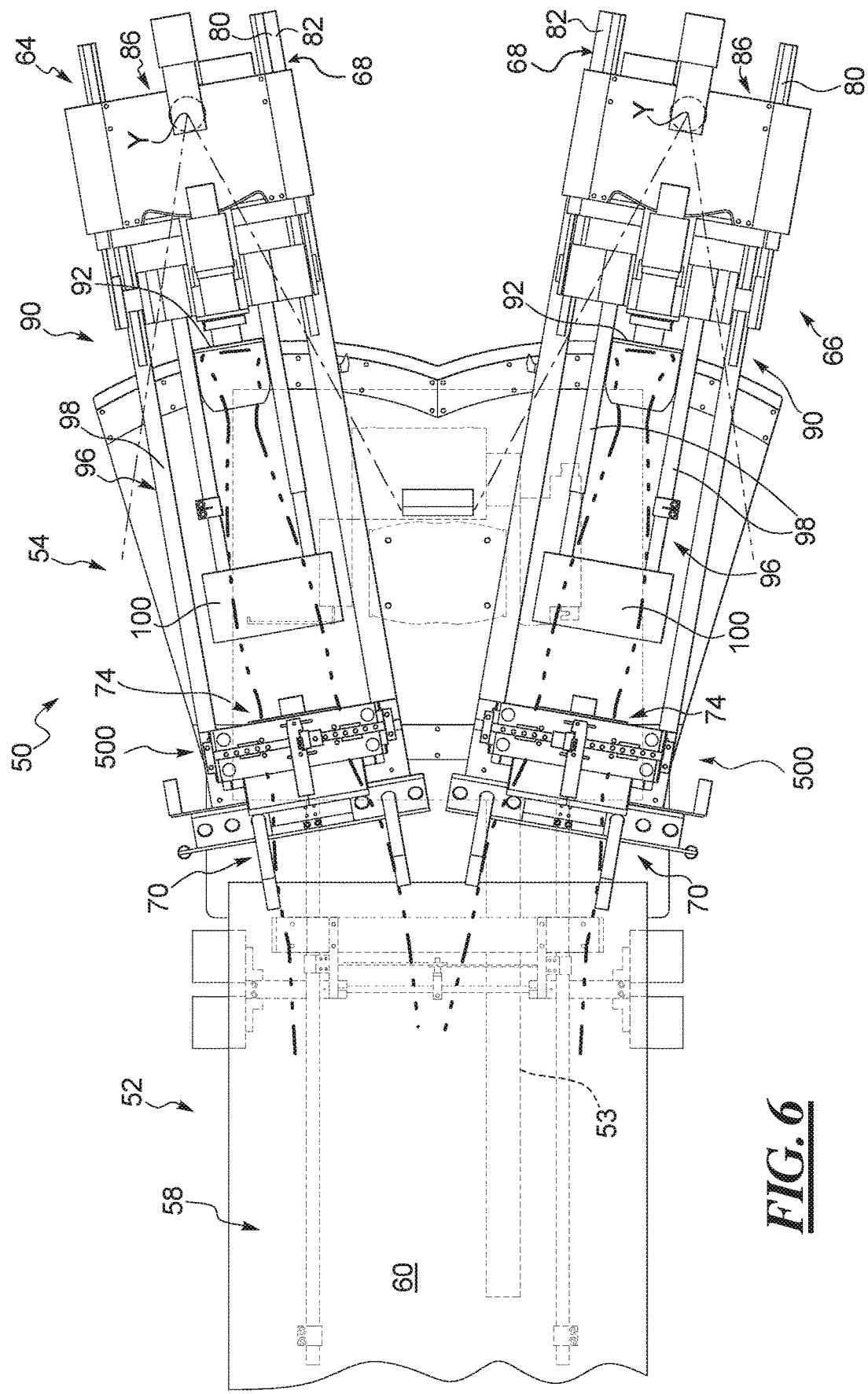
FIG. 6 shows a top view of the robot of FIGS. 2 and 5 and illustrates varus-valgus motion about the Y-axis of the tibia positioning assembly of each of the left and right leg portions.
Figure 7:
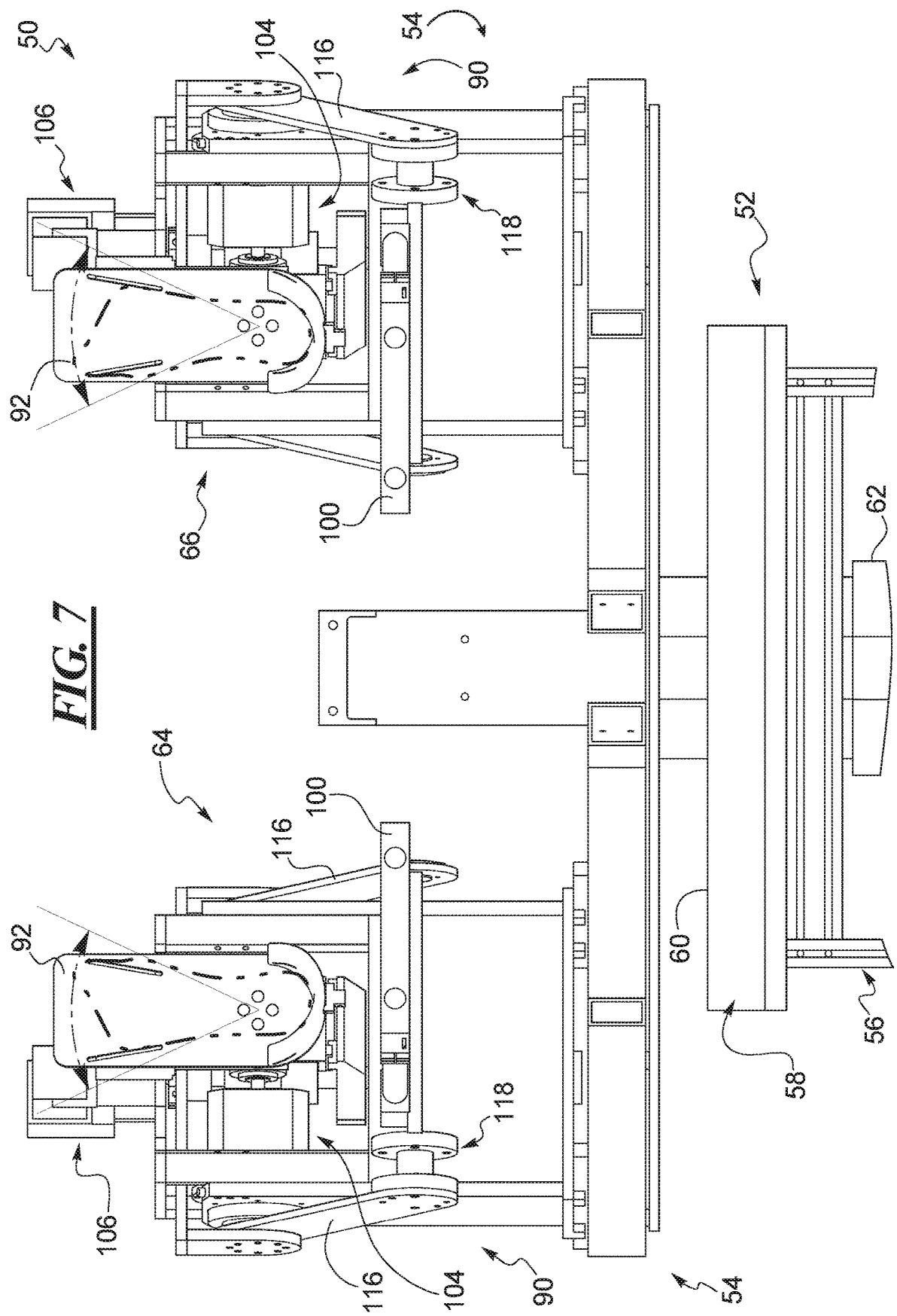
FIG. 7 shows an end view of the robot of FIGS. 2 and 5 as viewed from the left-hand side in FIG. 1 and illustrates internal-external rotation about the Z-axis of each of the left and right leg portions.

As shown in FIGS. 3, 6, and 7, the Y-axis drive 106 may include a second motor, which may also be an electric motor, a gearbox, and an output shaft that is driven by the motor and gearbox. A Y-axis torque transducer 148 is fixed to the output shaft for rotation therewith about the Y-axis. As shown in FIG. 6, the Y-axis drive 106 is configured to conduct a Varus-valgus or V-V test on a patient's knee. Position sensors may be applied to appropriate locations on the right leg of the patient. The Y-axis drive 106 imparts force about the Y-axis to initiate Varus-valgus motion in the tibia part of the knee joint relative to the fixed femur part of the knee joint of the patient, as shown in FIG. 6. The motor may reversibly rotate the output shaft through an arc about the Y-axis. The Y-axis torque transducer 148 measures the applied torque at the output shaft caused by the load applied to the foot plate 92 as the foot plate 92 pushes the patient's tibia medially or laterally relative to the femur. Motion (or position) and load data may be collected by a processor from the sensors relative to the motion in the patient's leg and from the Y-axis torque transducer 148 relative to the torque or applied forces.

The above-described Varus-valgus movement components of the tibia positioning assembly 90 may also vary considerably from the example shown and described herein. The mechanisms or devices that are used to secure a patient's leg to the tibia rods 98 and to the foot plate 92, if and when needed for testing, may also vary.

As shown in FIGS. 3 and 7, the Z-axis drive 108 may include a third motor, which may also be an electric motor, a gearbox, and an output shaft that is driven by the motor and gearbox. The Z-axis drive rotates the footplate 92 about the Z-axis when conducting a rotation test on a patient's knee. A Z-axis torque transducer 168 is fixed to the output shaft of the Z-axis drive 108 for rotation therewith. The foot plate 92 is secured to the torque transducer 168 for rotation therewith. Thus, as the output shaft is reversibly rotated by the motor and gearbox about the Z-axis, as shown in FIG. 7, the foot plate 92 will all rotate about the Z-axis.

As shown in FIGS. 3 and 7, the Z-axis drive 108 is configured to conduct an internal and external rotation test or simply a tibia rotation test on a patient's knee. Position sensors may be applied to appropriate locations on the right leg of the patient. The Z-axis drive 108 imparts force about the Z-axis to initiate rotation motion in the tibia part of the knee joint relative to the fixed femur part of the knee joint of the patient, as shown in FIG. 7. The motor may reversibly rotate the output shaft through an arc about the Z-axis whereby the torque transducer 168 is rotated through the same arc. This in turn moves, i.e., rotates the foot plate 92 about the Z-axis. Movement of the foot plate 92 in this manner rotates the patient's lower leg internally and externally relative to the femur. The Z-axis torque transducer 168 measures the applied torque caused by the load applied at the foot plate 92 as the foot plate rotates. Motion (or position) and load data may be collected by a processor from the sensors relative to the motion in the patient's leg and from the Z-axis torque transducer 168 relative to the torque or applied forces.

The above-described rotation movement components of the tibia positioning assembly 90 may also vary considerably from the example shown and described herein. The mechanisms or devices that are used to secure a patient's leg to the foot plate 92, if and when needed for testing, may also vary.

In use, a patient lies on the padded surface 60 of the patient platform 58 on the table assembly 52 as shown in FIG. 2. The patient's knees are positioned to engage the knee stabilizers 74, the patient's thighs are positioned to engage the thigh immobilizers 70, the patient's feet are positioned to engage the foot plates 92, and the patient's calves are positioned to engage the tibia rods 98. The patient may then be secured to the foot plates, to the knee stabilizers, and to the thigh stabilizers for testing and evaluation. The patient's calves or tibias may also be secured to the tibia rods 98 and/or the calf plates 100, as needed for specific testing. Movement of the lower leg of the patient may be detected by non-invasive systems utilizing sensors or markers that are attached to the skin, including but not limited to optoelectronic, ultrasonic, and electromagnetic motion analysis systems. In one example, the RKT apparatus 50 may be configured so that the patient's knees are flexed to about 30 degrees between the femur and the tibia. However, the tests or evaluations may also include the additional capability to flex the knee from 0 to 90 degrees to allow for similar tests (such as the examples above) done for different degrees of knee flexion.

Any one of the X-, Y-, and Z-drives may be decoupled from any of the other two. In the disclosed example, each of the three drive assemblies may be operable with one or more of the other at the same time or may be decoupled from each of the other two and be operable independent of the other two. In other examples, two or more, and perhaps all three of the drives may be mutually coupled relative to one another such that movements are substantially simultaneously imposed upon the patient's legs during use of the RKT apparatus.

The aforementioned sensors may be provided on the legs of a patient, in the power lines of the RKT apparatus, and/or on the X-, Y-, and Z-drives to obtain desired position or location data as the lower leg is moved during testing and evaluation. The degree of movement of the patient's legs in the A-P test, the V-V test, and/or the rotation test may be measured by detecting the movements of the parts of the apparatus, the rotation of the drives, and/or the actual movements of the patient's legs. The torque encountered during each test and over the range of motion applied during each such movement may also be measured, suitably calibrated to the limb movement, and recorded.

Testing and evaluation of knee joints using the RKT apparatus 50 may be inconsistent from patient to patient, from doctor to doctor, and from test procedure to test procedure by the same doctors and/or on the same patients. Such inconsistency is created at least in part because each stage or step of the setup and testing procedures may introduce error into the data. Such inconsistency may also be caused in part by residual movement of the patient's femurs, which are retained by the thigh immobilizers 70 and knee stabilizers 74. The cumulative error may become quite substantial and thus significantly affect the accuracy of the test results.

Detecting and accounting for residual movement of the patient's femur during testing may reduce cumulative error. Compensating for residual movement may be combined with other techniques directed to improving consistency. For instance, providing a consistent method or procedure to get a patient set-up in the RKT apparatus 50 has been determined to aid in producing more consistent test results and reducing error in the data. Further, providing a consistent method or procedure to set up or initialize the robot 54 of the RKT apparatus 50 prior to testing a given patient has also been determined to aid in producing more consistent test results and reducing error in the data.

Figure 8:
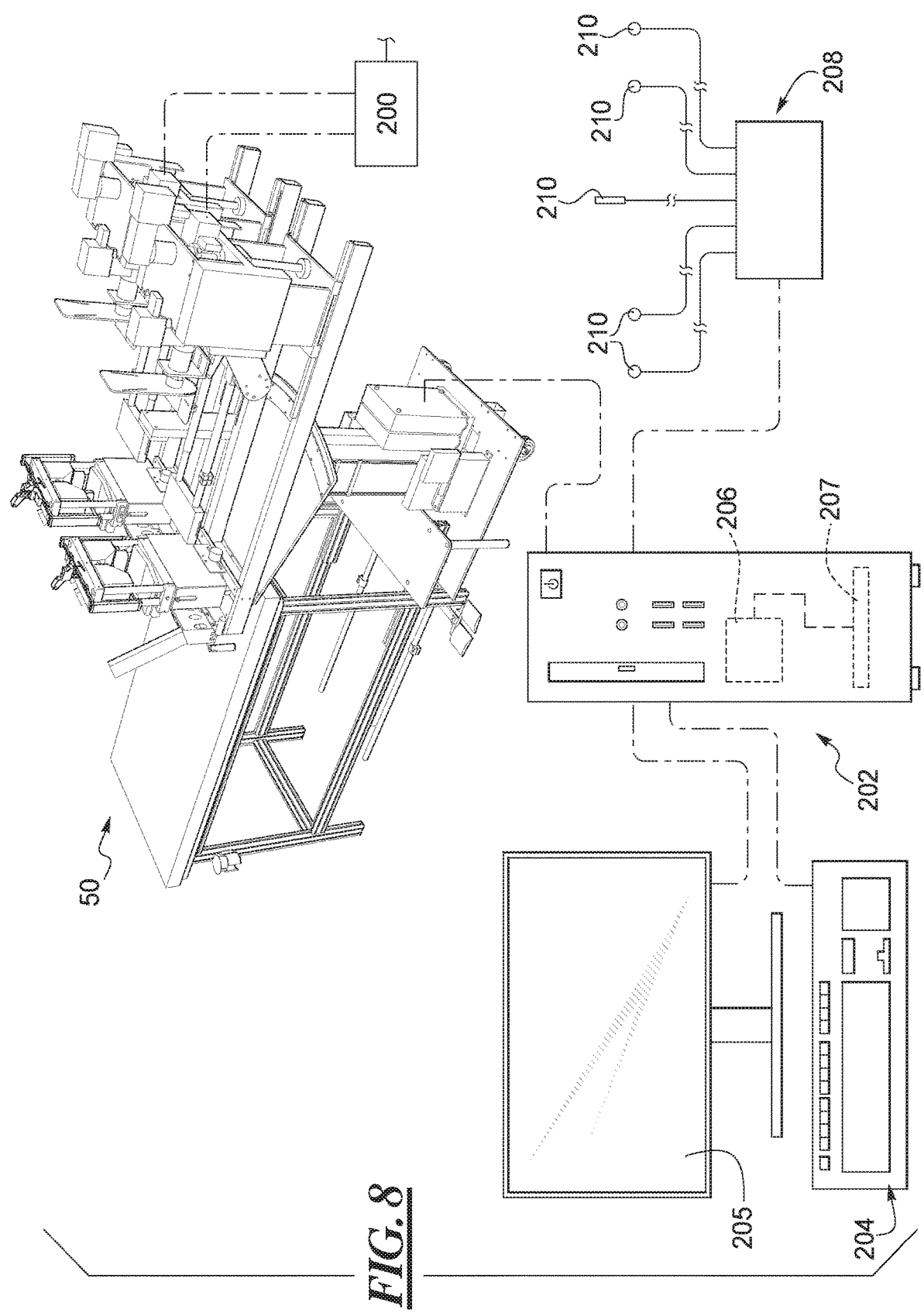
FIG. 8 shows an environment view of the RKT apparatus of FIG. 1, or of a system utilizing the RKT apparatus of FIG. 1.

As shown in FIG. 8, the robot 54 of the RKT apparatus 50 may be part of a system and connected to a power source 200 to operate the robot. The power source 200 may be a typical 120/220 volt AC grid, a converted direct current power source, a stand-alone power source such as a generator or battery, or the like. The robot 54 of the RKT apparatus 50 may also be connected to a programmable electronic device or network of devices, such as a computer 202 or a computer network, a network server, or the like that are part of the system. In any case, the computer 202 may have or may be connected with an input device 204, such as a keyboard, a user display 205, such as a monitor or screen, a memory 206, and a processor 207. The robot 54 and/or computer 202 may also be coupled to a sensor or tracking system 208. The tracking system 208 may utilize one or more individual sensors 210 that are configured to detect or determine spatial positioning or location of the sensor at a point in time. The types of sensors 210 and tracking system 208 may employ electromagnetic (EM) sensors, electromagnetic field (EMF) sensors, or other suitable sensor technology.

In the example described above, the X-, Y-, and Z-drives 104, 106, 108 may be connected to and operable by the computer 202. The computer 202 may be programmed to receive and store load or torque data from the X-, Y-, and Z-drives 104, 106, 108 and to receive and store spatial position data from the sensors 210 and tracking system 208. The processor 207 may be programmed to calculate information and provide feedback related to knee laxity, based on the data. The information and feedback may be provided to the examiner on the display 205. The knee laxity information and feedback may relate to anterior-posterior movement, Varus-valgus movement, and/or tibia rotation movement, as described above. As represented in FIG. 9, the set-up of the patient relative to the RKT apparatus and, e.g., the robot 54, may be performed or specified as disclosed herein to aid in rendering the test data, information, and feedback more consistent and more accurate. Likewise, also as shown in FIG. 9, the set-up of the robot 54 prior to undertaking any testing may also be performed or specified to aid in rendering the test data, information, and feedback more consistent and accurate.

FIG. 10 is a flow diagram of a set-up method in accordance with one example. In this example, the method combines steps relating to setting up the patient relative to the RKT apparatus and setting up the robot 54 prior to testing. In other examples, the method may include only steps to set-up the patient relative to the RKT apparatus 50 and robot 54. Likewise, the method may include only steps to set up the robot 54 prior to testing.

In act 300, the RKT apparatus 50 is turned on or powered up. For example, the computer 202, the tracking system 208 including the sensors 210, and the robot 54 are each started, turned on, or powered up. The RKT apparatus is accordingly set up and running to prepare the apparatus for use.

In act 302, the drives or motors of the robot 54 are leveled. In the disclosed example, to do so, the motors of the corresponding X-, Y-, and Z-drives 104, 106, 108 may be precisely leveled relative to a horizontal or vertical reference or referencing a leveling device. For example, a portion of the tracking system 208 may be used to precisely level the motors. Alternatively, the motors may be leveled manually or mechanically, e.g., via an inclinometer. The act 302 provides and defines a consistent, repeatable starting point for the tibia positioning assembly 90 that may be achieved prior to each test using the RKT apparatus 50.

In act 304, the torque in each of the drives or motors is zeroed. In the disclosed example, each of the motors of the drives 104, 106, 108 is zeroed. The motors may thus be adjusted, positioned, or re-set to a condition where the torque transducers read zero torque or where the output shafts are under no torque. The act 304 provides and defines a consistent and repeatable starting condition, e.g., a neutral or zero torque starting point for each drive or motor prior to each test using the RKT apparatus 50.

In act 306, the positioning system 53 is utilized to aid or assist a patient in getting up onto the table assembly 52 and in positioning the patient's lower extremities or lower legs relative to the robot 54 for testing and evaluation. For example, the positioning system 53 and the robot 54 may be moved to an extended position slid away and spaced from the distal edge of the table assembly 52. The patient may then be situated in an upright position between the robot 54 and the table assembly 52. The patient may then step up on the step 57, if needed, onto and then lie down on the table assembly 52. The robot 54 may be returned toward and beneath the patient's legs.

In act 308, the abduction angle of the patient's femurs is adjusted relative to their hips. In other words, the patient moves or is positioned on the table assembly 52 and on or in the tibia positioning assemblies 90 so that their femurs are at a desired abduction angle. This adjustment may be done in order to adjust the abduction angle of the patient's femurs so that the patient's femurs are neutrally aligned with their hips. Alternatively, the tibia positioning assemblies 90 may be in a fixed abduction orientation, such as at a fixed 30-degree angle relative to one another, as noted above. The thigh stabilizers 70 may then be adjustable laterally as mentioned further below so that the patient's femurs may be neutrally aligned with their hips. The act 308 positions the patient's femurs in a consistent, repeatable, and comfortable manner relative to the robot 54. In some cases, the femurs are neutrally lined up with the patient's hips so as to limit stress on the patient's upper legs and hips during a test and to create a repeatable and consistent orientation of the lower legs relative to the femurs of the patient.

In act 309, the position of the robot 54 is adjusted relative to the patient's trunk and table assembly 52 in the horizontal and vertical direction using the positioning system 53 to position the patient's knees in a desired degree of flexion. Here, the vertical movement of the column lift 62 and horizontal movement of the positioning system 53 may be done simultaneously or independently to adjust the degree of flexion in the patient's knee. Implementing the act 309 allows the clinician to position the patient's knees in the desired flexion in a range of 0 to 90 degrees.

In act 310, the patient's knees are centered relative to the respective knee stabilizers 74. For example, as shown in FIGS. 3-5, each knee stabilizer 74 is mounted on or to a support base 312, which is positioned under and coupled to the lower knee clamping element 78*b* and attached to the guide rails 82. The upper knee clamping elements 78*a* may be removed for this step. The support base 312, and thus the knee stabilizer 74, is side-to-side adjustable. The knee stabilizer 74 may incorporate a locking element 316 that is configured to selectively secure or release the knee stabilizer 74 relative to the slide track. In the disclosed example, to center the knee stabilizers 74 on the patient's knees, one may release the locking elements 316 and slide the knee stabilizers side-to-side. The knee stabilizers 74 may be moved to laterally center the corresponding posterior knee pads 79 on the lower knee clamping elements 78*b* under the knees of the patient. The construction of the support base 312 and locking elements 316 may vary considerably and still function as intended to provide side-to-side adjustability of the knee stabilizers 74. The act 310 may define a consistent and repeatable position for the patient's knees relative to the tibia positioning assemblies 90 generally in the X-axis direction. The act 310 may also center the patient's knees within the knee stabilizers 74 so that, when ultimately clamped onto the knees of the patient, each knee is centered among the pads 79 and thus securely retained in position to inhibit movement of the femur and patella once clamped in the respective stabilizer.

In act 320, the thigh immobilizers 70 are adjusted to secure the patient's femurs in place. In the disclosed example, as shown in FIG. 4, each thigh immobilizer 70 has a primary mechanical adjustment device. Each thigh immobilizer 70 is mounted to a support block 325 carried on a plate 322 attached to the guide rails 82. Each thigh immobilizer 70 may also include a locking mechanism for each of the clamping elements 72. Each clamping element 72 has a truck 324 that carries a paddle 73 extending upward from the truck. In the disclosed example, the clinician may release the locking mechanisms and slide the thigh clamping elements 72 and trucks 324 laterally and independent of one another. The construction of the locking mechanisms may vary considerably and still function as intended to provide sideto-side independent adjustability of the thigh clamping elements 72 on each of the thigh immobilizers 70. The trucks 324 and thigh clamping elements 72 may optionally include a secondary distinct mechanical adjustment device as well. This feature may aid in allowing the thigh immobilizers 70 to accommodate a wider range of patient leg sizes from small children to large adults. In this example, each truck 324 has multiple bores 337 that are laterally spaced apart and open to the top surface of the truck. Each paddle 73 has a corresponding peg or pin 334 protruding downward from the body of the paddle. The peg 334 of each paddle may be selectively inserted into any one of the multiple bores 337 in the corresponding truck 324. By choosing different arrangements of the bores 337, and without moving the trucks 324, the adjacent paddles on one of the thigh immobilizers 70 may be mounted to the trucks 324 in a plurality of different positional arrangements. Depending on which of the bores 337 are selected, the paddle spacing may be altered and/or the paddles may be shifted to the left or to the right, if desired or needed, also without having to move the trucks 324. This secondary adjustment scheme allows for greater versatility in setting up a patient. Any type of locking mechanisms, such as a cam lock type device, may be used to also secure the pegs 334 in the bores 337, if desired, or a separate retention means, if any, may also be used to retain the paddles to the trucks 324.

Once the patient's knees are correctly positioned, according to the act 306, and the knee stabilizers 74 are centered according to the act 310, the thigh immobilizers 70 may be adjusted, set, and clamped onto the patient's thighs. Each thigh clamping element 72 may be positioned or secured such that the medial and lateral clamping elements apply substantially equal pressure to the thigh. The thigh clamping may permit a consistent and repeatable position for the patient's thighs relative to the tibia positioning assemblies 90, also generally in the X-axis direction. The thigh clamping may then securely clamp the patient's thighs in place with the thigh immobilizers 70. During testing, it is useful that the femur position for each leg of a patient is securely retained to prevent lateral movement and femoral rotation once the thigh immobilizers 70 are adjusted and locked in place.

In act 340, each knee stabilizer 74 is clamped onto the patient's knee or patella. In the disclosed example, as depicted in FIGS. 3-5, the framework 76 of each knee stabilizer 74 may include a pair of guide posts 342 on each side of the stabilizer. The guide posts 342 may be fixed to the upper knee clamping element 78a and may depend down from the element. Free ends 344 of the guide posts may be received in and slide through a corresponding pair of holes 346 on each side of the lower knee clamping element 78b. The upper and lower clamping elements 78a, 78b are adjustable vertically relative to each other, as noted above, by sliding the upper clamping element 78a and guide posts up and down relative to the lower clamping element 78b, which is fixed to the support base 312. A fixing screw 348 in this example extends transversely into each side of the lower clamping element 78b between the pair of holes 346. The fixing screw 348, when rotated in one direction may reduce the diameter of the holes 346 to clamp onto and lock guide posts 342 and, when rotated in the opposite direction, may increase the diameter of the holes to release the guide posts. With the guide posts 342 released, the upper knee clamping elements 78a (and guide posts 342) may be removed from the lower knee clamping element 78b so that the patient's knees may be readily positioned on the lower clamping elements, as noted for the step at block 306. Once the knees are properly positioned after the step at block 306, the upper knee clamping element 78a may be replaced on the lower knee clamping element 78b any time before block 340.

At this point, the locking elements 316 on the knee stabilizers 74 are still released so that the knee stabilizers 74 are free to slide or move laterally. Also at this point, the upper knee clamping element 78a may now be or should already have been reinstalled on the lower knee clamping element 78b. The upper knee clamping element 78a is then clamped downward so that the pads 79 on the upper knee clamping element press down against the patella of the knee. The downward clamping force should achieve a predetermined or desired force, such as 30 lbs., and equal pressure may be applied to both the medial and lateral sides of each knee stabilizer 74. The knee stabilizers 74 may then be secured in this clamping condition. In this example, the fixing screws may be rotated to secure the guide posts 342. A force gauge or other suitable method and/or device may be used to achieve the desired downward clamping force applied by the knee stabilizers 74 on each patella of the patient. Once the knee clamping elements 78a are clamped and locked, the knee stabilizers may then be locked in place laterally by actuating the locking elements 316. The knee clamping step may thus securely clamp the patient's knee at the patella in the knee stabilizers 74. During testing, it is useful that the lower end of the femur and the patella are securely retained to minimize or reduce vertical movement at the patella once the knee stabilizers 74 are adjusted, clamped down, and locked.

In act 350, the patient's feet are placed against the foot plates 92. In the disclosed example, the tibia positioning assemblies 90 are drawn toward the patient's feet by sliding the assembly along the tracks 80 on the sub-frames 68. Once the feet are in contact with the two foot plates 92, the tibia positioning assemblies 90 are in a testing position relative to the patient's feet and lower legs. When the feet are properly positioned, appropriate straps (not shown) may be used to secure the feet to the foot plates 92. The act 350 may provide a consistent and repeatable mechanism to properly position the tibia positioning assemblies 90 along the sub-frames 68 relative to a specific patient. The act 350 may also secure the patient's feet to the foot plates and thus to the drive system of the tibia positioning assemblies.

In act 360, the tibia positioning assemblies 90 are locked in place. In the disclosed example, each tibia positioning assembly 90 may be locked in the set or adjusted position that is achieved at the step of block 350. This will lock the tibia positioning assemblies 90 at the adjusted position accommodating the particular patient being set up. A ruler or other indicia or markings may be provided on or along one of the lengthwise parts of each sub-frame 68, such as along one of the rails 82. The rulers may be configured to identify the length of the lower legs of the patient being set up, based on the position of the tibia positioning assemblies 90 along the tracks 80 or the sub-frames 68. This measurement may be recorded for each specific patient and may then be utilized to set up the robot 54 for a particular patient each time the patient is tested. This helps to ensure that the RKT apparatus 50 is set up the same way for the same patient each time the patient is tested. The act 360 may thus aid in providing a fixed, consistent, and repeatable set-up position for the tibia positioning assemblies 90 for each patient.

In act 370, the patient's feet are rotated to a desired initial rotational orientation. In the disclosed example, each foot plate 92 may be manually rotated to a desired position determined by the orientation of a part of the patient's foot or a part of the foot plate. For example, the patient's foot could be positioned with the toes up and perpendicular to the floor beneath the RKT apparatus. More specifically, the starting orientation may be to orient the second toe on each foot point vertically perpendicular to the floor. This initial foot rotation position may instead be established by moving the Z-axis motor into a neutral zero-torque position to find a true resting position for the patient's feet. The act 370 may thus define a consistent and repeatable starting orientation for the foot plates 92.

In act 380, each tibia rod device 96 is properly positioned under the patient's calves. In the disclosed example, each tibia rod device 96 may be length adjustable to retract or extend the calf plate 100 to a desired position under the corresponding calf of the patient. Once in the desired position, the calf plate is in a testing location or an AP test location relative to the patient's leg. A ruler or other indicia or markings (not shown) may be provided along part of the tibia rod device 96 to help determine the proper or desired position for the calf plate 100 (see FIG. 5). If the desired position of the calf plate 100 for each patient is to be three-quarters (¾) of the way up the leg from the patient's heel, the ruler (not shown) may be a ¾ scale version of the ruler, which defines the patients leg length. Thus, by selecting the same measurement on both rulers, the position of the calf plate 100 is assured on each tibia positioning assembly 90 for each patient. Such measurements help to ensure that the patient set-up is as consistent as possible. The act 380 may thus provide a mechanism to ensure repeatable and consistent positioning of the tibia rod device 96 so that the AP test is always conducted at the same relative location on each patient's legs.

In act 390, tibial sensors 210 are placed on the patient's legs. In the disclosed example, sensors 210 are positioned on the flat region of the bone that is just medial to the tibia tubercle on each leg. The sensors 210 are then strapped into place at this location. The location is selected for the sensors 210 because this region has the least amount of soft tissue between the sensor and the bone. This location will thus help during testing to limiting the degree of movement of the sensors caused by the soft tissue moving relative to bone. In one example, round sensor holders may be used to retain each sensor 210 in order to inhibit or prevent the sensors from rocking, due to compression of the calf muscle during testing.

In act 400, the desired test or tests are then conducted on the patient that has been set up in the RKT apparatus 50. These tests may include the anterior-posterior or AP test, the Varus-valgus or V-V test, and the medial and lateral rotation test. Data is collected during the testing by the computer and may be evaluated by the computer in order to render a diagnosis for the knee joint being tested with respect to knee laxity and joint play.

Fewer, additional, or alternative set-up procedures may be utilized during testing or prior to testing in addition to those discussed above. For example, during AP testing, one or more straps may be utilized to secure the patients legs to the tibia rod devices 96. This may be to ensure that the tibia rod devices may both push up in an anterior direction on the patient's legs and pull down in a posterior direction on the patient's legs during testing. Once the AP test is completed, these straps may be removed and the tibia positioning rods may be moved out of the way prior to conducting a rotation test or a Varus-valgus test on the patient. In another example, during a Varus-valgus test, additional pads may be pushed into the knee stabilizers 74 between the medial and lateral sides of the patient's knees and the framework 76. Such pads may help to minimize medial or lateral movement of the knee under the clamp and minimize axial rotation during the Varus-valgus test. Alternatively, the knee stabilizers may be fitted with additional elements, such as adjustable medial and lateral constraints (to replace the additional pads) and/or a patella sensor to further eliminate error during testing, as described below. These added features may further reduce error in the collected data.

In some cases, the knee is flexed to about 30 degrees during the above tests (AP, Varus-valgus, or rotation). However, the tests or evaluations may also include the additional capability to flex the knee from 0 to 90 degrees to allow for similar tests (such as the examples above) done for different degrees of knee flexion.

The femur is encased in soft tissue such that a sensor on the skin will not follow its motion. To get around this problem, the joint stabilizer, which is the knee stabilizer 74 in this example, is intended to rigidly clamp the femur through the soft tissue to the RKT apparatus 50 during testing. The knee stabilizer 74 pushes the patella down into the groove of the trochlea helping to lock the femur in rotation. The pads 79 of the knee stabilizer 74 may allow 30 lbs. force of compression while maintaining the patient in a reasonable comfort zone. Once the patient's leg is secured or clamped by the knee stabilizer 74, it was assumed that the femur does not move and a device-based coordinate system is developed as the femoral coordinate system for testing and evaluation.

However, during testing, a patient's femur and/or patella may move rather substantially, even with the knee joint and femur held stationary by the knee stabilizer 74. For instance, during the anterior/posterior or AP test, further compression of the pads 79 may occur, which allows displacement of the femur to occur. The displacement may include anterior/posterior translation and/or medial/lateral translation of the femur. Still other translations or displacements of the femur may occur. Such translation (or other displacement) of the femur is added to the translation of the tibia. Because the clinician is only interested in the translation of the tibia, compensation for this residual translation of the clamed femur is useful. The residual translation may otherwise hinder the accuracy of the data retrieved.

Figure 11:
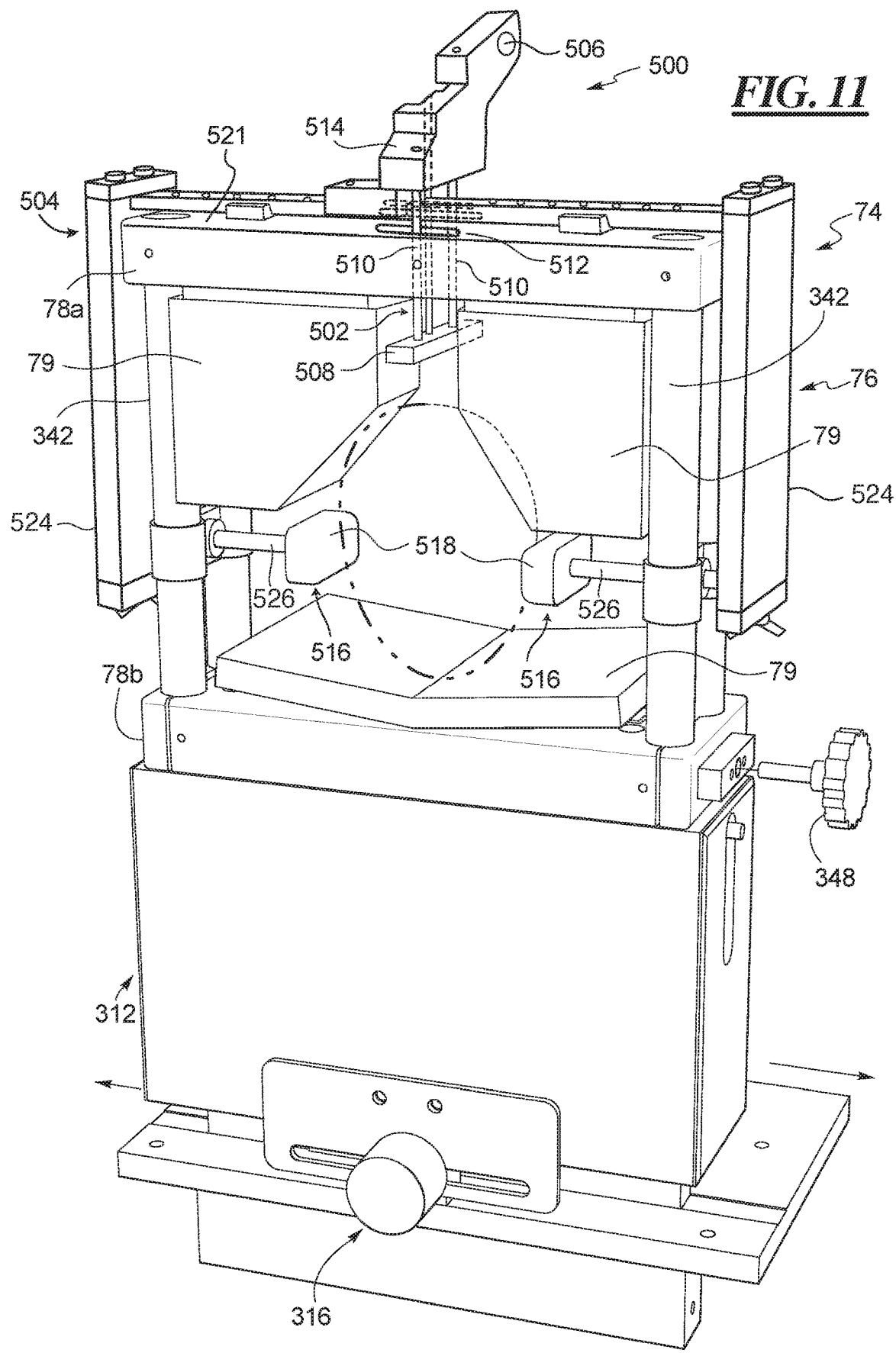
FIG. 11 is a perspective view of the knee stabilizer of the right leg portion of FIG. 3 to depict a bracket assembly of the knee stabilizer in accordance with one example.
Figure 12:
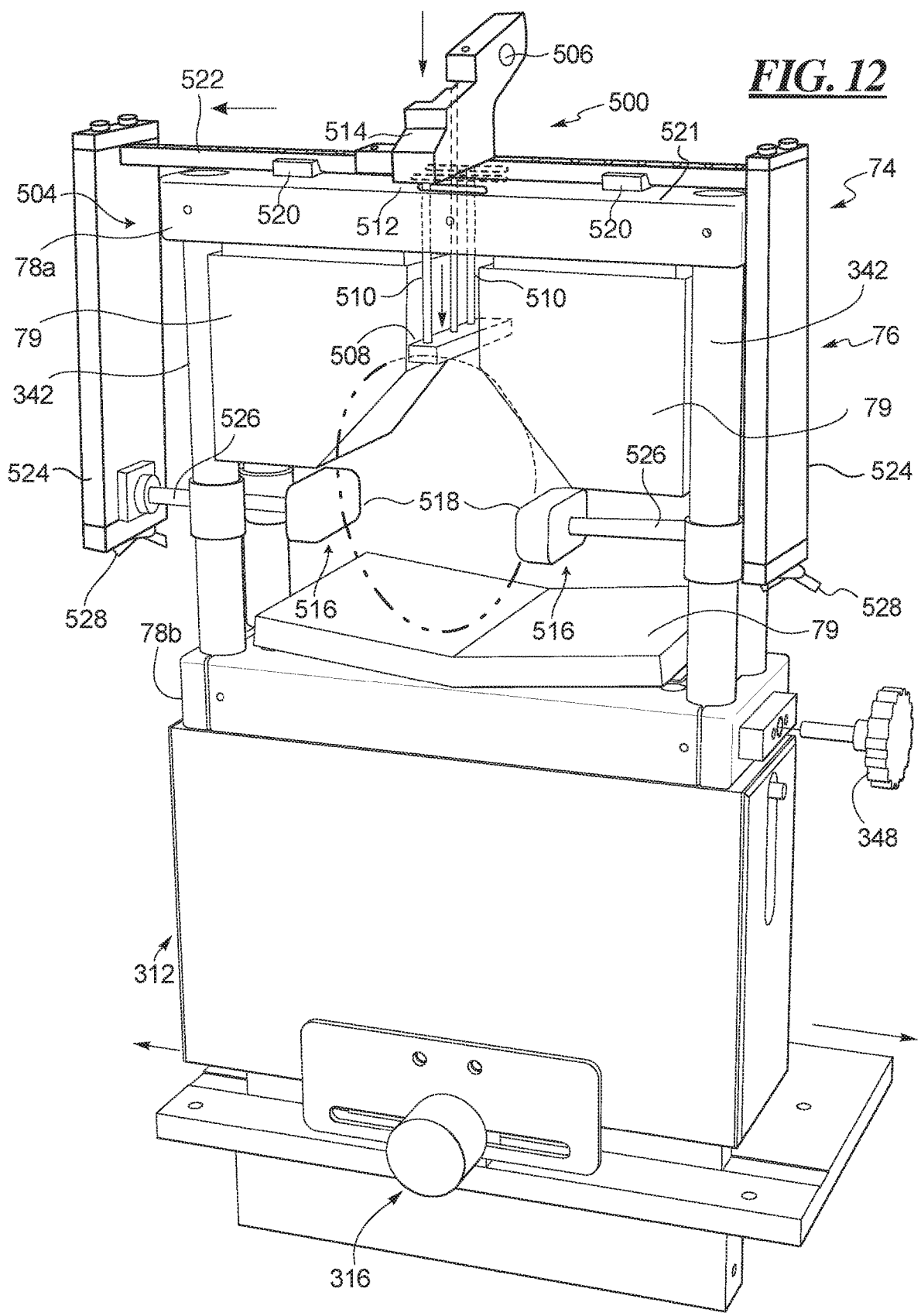
FIG. 12 shows the bracket assembly of the knee stabilizer of FIG. 11 in contact with the knee of the patient and after displacement of the bracket assembly arising from residual movement of the knee during testing.

With reference to FIGS. 11 and 12, a joint testing apparatus (e.g., RKT apparatus) includes a sensor system 500 to measure or monitor the residual translation or other displacement (e.g., rotation). In the knee testing example shown, the sensor system 500 is disposed on top of the patella to move (e.g., float) with the patella through the knee stabilizer 74. The sensor system 500 includes a float assembly 502 to monitor anterior-posterior translation of the joint and a bracket assembly 504 to monitor medial-lateral translation of the joint. In knee joint cases, the float assembly 502 may be configured to engage the patella of the knee, i.e., as a patella monitoring assembly. The bracket assembly 504 may be configured to engage the condyles of the knee, i.e., as a condyle monitoring assembly. Both the float assembly 502 and the bracket assembly 504 are supported by, and moveable relative to, the frame of RKT apparatus. As described above, the frame is configured to support the knee (or other joint) while facilitating the application of force (e.g., by one or more drives also supported by the frame) away from the joint (e.g., distal to the foot) for evaluation thereof.

In the example shown, the float assembly 502 and the bracket assembly 504 are carried by a clamp disposed between the frame and the subject. In this case, the clamp is or includes the upper knee clamping element 78*a*. The clamp is configured to stabilize a part of the joint while a bone of the subject is manipulated by a drive of the RKT apparatus. Other types of clamps may be used in connection with the sensor system 500.

The sensor system 500 may measure the residual translation of the femur during a test. Accounting for the residual translation provides more accurate test results. For instance, the true anterior/posterior position of the femur during the test may thus be represented by the acquired data. In some cases, data indicative of the residual translation is used to develop a more accurate femoral coordinate system, e.g., a device-based femoral coordinate system, resulting in more accurate test and evaluation data. Residual anterior and posterior translation of the femur during the test caused by compression of the pads within the clamp and/or other causes (e.g., possible loosening of the clamp) may thus be accounted for in the analysis. Thus, more accurate tibial motion (e.g., tibial anterior-posterior translation) may be identified.

The sensor system 500 includes a sensor 506 coupled to the float assembly 502 and the bracket assembly 504 such that the sensor 506 is moved by displacement of the assemblies 502, 504 relative to the frame during the evaluation of the joint. The sensor 506 is configured to generate a signal indicative of the displacement. In some cases, the sensor 506 is an electromagnetic sensor. In the example shown, the sensor 506 includes a sensing unit disposed within an opening in the sensor housing 514. Other sensing unit-housing arrangements may be used. The sensor 506 may be similar to those used to detect other position data. Other types of sensors may be used, including, for instance, optical, magnetic, and/or mechanical sensors. For instance, a variety of linear digital scales (e.g., encoders) may be used. In optical sensing cases, the sensor 506 may include a camera or other optical detection device or sensor carried by, or disposed in or on, the sensor housing 514, or otherwise coupled to the bracket assembly 504. The optical sensor may implement optical tracking of the displacement of the bracket assembly 504 by reading or otherwise detecting lines of a ruler or other scale mounted on a static component of the knee stabilizer 74, such as a platform 521 or other frame element. In magnetic sensing cases, the sensor 506 may include a caliper or other instrument configured to read a magnetic strip or other element. In mechanical sensing cases, the sensor 506 may include a dial indicator coupled to the bracket assembly 504. The sensor 506 may include other types of optical, magnetic, and mechanical tracking arrangements. For instance, in each of these sensing arrangements, the sensor 506 may include the detecting (or tracking) element, the detected (or tracked) element, or other element used to generate a signal indicative of the displacement. In still other cases, the motion may be detected using reflective markers (e.g. stickers or dots) placed on, for instance, the patella. For example, the sensor 506 may include one or more retroreflective markers disposed in a cluster or other arrangement across the sensor system 500. Such markers may be used in conjunction with linear digital scales or other elements of the above-referenced tracking techniques. In the example shown, the sensor 506 is a single sensor used by both the float assembly 502 and the bracket assembly 504. In other cases, multiple sensors are used. For instance, separate sensors may be used to monitor residual motion in different directions (e.g., multiple sensors for the different translations).

The sensor 506 is configured to generate a signal indicative of the displacement of the float assembly 502 and/or the bracket assembly 504. The sensor system 500 may include a lead or other connection that provides the signal as an output. The output may be provided to the computer 202 of the RKT apparatus system. Thus, data form the sensor system 500 may be collected during testing to account for the undesirable residual femur translation.

The computer 202 (FIG. 8) and/or another computer or other processor may be configured to adjust the position data for the test based on the data from the sensor system 500. For example, the position data from an AP test, a varus-valgus test, and/or an internal-external rotation test is adjusted. In those and other cases, a processor, such as the processor 207 (FIG. 8) of the computer 202, may be configured to adjust position data for the tibia in accordance with data indicative of the displacement to compensate for the residual movement of the stabilized part of the knee during the joint evaluation. Instructions for configuring the processor 207 may be stored in the memory 206 (FIG. 8) and/or another memory.

With reference again to FIGS. 11 and 12, the float assembly 502 includes a joint contacting end 508, which may be a plastic part, and which may rest via gravity (FIG. 12) on top of the patella. Double-sided tape or other adhesives may alternatively be used. Rods 510 are attached to the joint contacting end 508 and extend through the upper knee clamping element 78a of the knee stabilizer 74. In the example shown, the rods 510 extend through respective slots 512 in the plate of the upper knee clamping element 78a. The rods 510 may then be connected to the housing 514 of the sensor 506. The housing 514 is carried on the upper knee clamping element 78a or another part of the knee stabilizer 74, as described below.

The float assembly 502 rises and falls with residual motion of the femur within the knee stabilizer 74. In this case, the residual motion includes motion in the AP direction. The residual motion displaces the joint contacting end 508 of the float assembly 502. Thus, in one example, the float assembly 502 is configured to account for translation in the AP direction. Monitoring the residual motion in the AP direction may be useful in connection with tests in which a drive of the test apparatus is manipulating the joint in the AP direction, i.e., the same direction as the residual motion. However, monitoring residual motion in the AP direction may also be useful in other tests, such as a varus-valgus test and an internal-external rotation test.

Residual motion in other directions may be alternatively or additionally monitored. In the example shown, the sensor system 500 is not limited to monitoring residual motion in the AP direction. The other directions may be different than the direction in which a drive is manipulating the joint during a test.

The sensor system 500 (and/or the knee stabilizer 74 or joint test apparatus) includes a bracket assembly 504 to monitor residual motion in one or more other directions. The bracket assembly 504 is configured to engage the joint. The bracket assembly 504 has a pair of ends 516. Each respective end 516 of the bracket assembly 504 may engage the medial and lateral sides of the knee. Each end 516 may include a pad 518. Each pad 518 may be configured to engage the respective condyle of each knee.

The engagement of the knee by the bracket assembly 504 allows the sensor system 500 to detect displacement of the knee (and/or femur) in a direction other than the AP direction. In the example shown, the displacement direction is translation in the medial-lateral direction. The displacement may be in a direction different than the direction in which a drive is configured to manipulate the tibia. For example, during AP testing, the X-axis drive 104 imparts force to initiate anterior-posterior motion of the tibia. Even though the femur is stabilized, the femur may be displaced or otherwise move in the medial-lateral direction. The displacement detected via the bracket assembly 504 is thus indicative of residual movement of the stabilized part of the joint during the joint evaluation.

As shown in FIG. 12, the residual motion causes the bracket assembly 504 to slide in the medial-lateral direction. In this example, the bracket assembly 504 includes a bar 522 slidably engaged with the frame of the test apparatus, e.g., the knee stabilizer 74. The bar 522 may be configured as a rail. The bar 522 supports the sensor 506. The sensor 506 is mounted on the bar 522 such that the displacement includes translation of the bar 522. The bar 522 is displaced within one or more linear bearings 520 mounted on the frame of test apparatus, e.g., the knee stabilizer 74. In the example shown, two linear bearings 520 are disposed on a platform 521 of the upper clamping element 78a.

The bracket assembly 504 further includes a pair of link posts 524 extending (e.g., downward) from the bar 522. The link posts 524 position the ends 516 of the bracket assembly 504 along opposite sides of the joint. A pair of arms 526 of the bracket assembly 504 extend laterally inward from respective link posts 524 toward a respective side of the opposite sides of the joint. The arms 526 may be configured as rods. The arms 526 terminate at the pads 518 disposed on the opposite sides of the joint.

The connections between the pair of arms 526 and the pair of link posts 524 may be adjusted during set up of the patient and the RKT apparatus. The connection adjustments modify a spacing between the pair of pads 518, thereby tightening or loosening the knee constraint. Adjusting the spacing clamps the pads 518 against the sides of the patient's knees. In this example, each arm 526 is slidable through a one-way clamp 528 (or spring device) that, in one position, securely restrains the rods and, in another position, releases the rods for adjustment. Alternatively or additionally, the arms 526 are or include threaded rods. In such cases, the threaded rods may have an adjustment knob at the ends opposite the pair of pads 518. The knobs may be turned in one direction to tighten the constraints and turned in the opposite direction to loosen the constraints. Wing nuts or other fasteners may also be used to secure the arms 526 in position and establish the clamp spacing. The constraints may be adjusted at various times prior to testing, such as when the knee stabilizer 74 is clamped to the knee at block 340 (FIG. 10).

Figure 13:
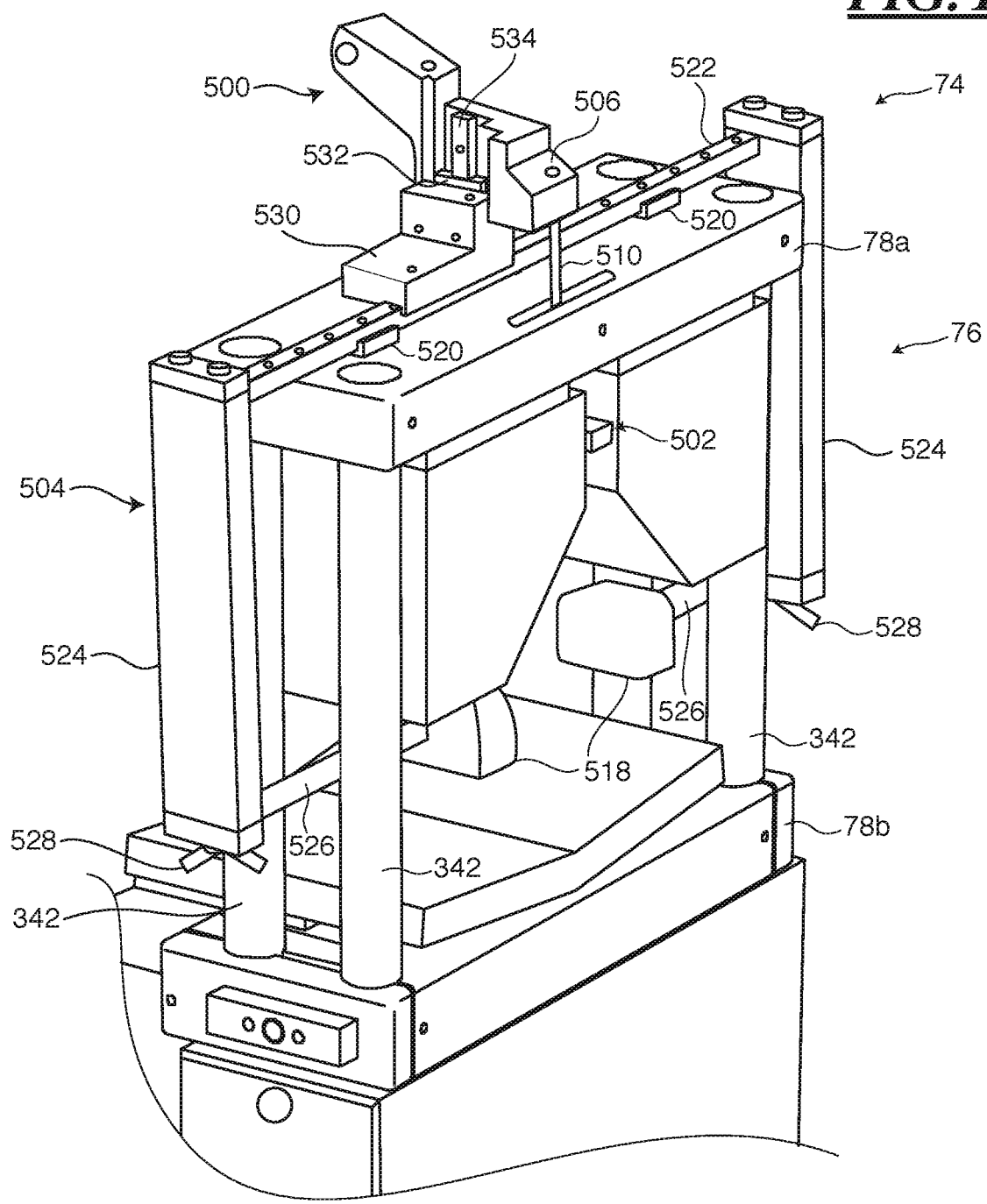
FIG. 13 is another perspective view of the knee stabilizer of FIG. 11 to depict a sensor mounting on the bracket assembly in accordance with one example.

With reference now to FIG. 13, the bar 522 and other aspects of the bracket assembly 504 may be configured to accommodate, and integrate with, the float assembly 502. The integration of the float assembly 502 and the bracket assembly 504 allow a single sensor (e.g., the sensor 506) to be used to measure the displacement of both the float assembly 502 and the bracket assembly 504. In the example shown, the rods 510 of the float assembly 502 extend from the sensor 506 on either side of the bar 522 to establish a contact point with the joint. The sensor 506 is slidably coupled to the bar 522 to allow displacement of the rods 510 and the sensor 506 as a result of the residual movement of the joint (e.g., movement of the femur or other clamped portion of the joint). To provide the slidable coupling, the sensor assembly 500 includes a bracket mount 530. The bracket mount 530 couples the sensor 506 to the float assembly 502 and to the bracket assembly 504. The bracket mount 530 is fixedly attached to the bar 522. The bracket mount 530 thus moves laterally with the bar 522 as residual motion of the joint displaces the bracket assembly 504 in the medial-lateral direction. A linear bearing 532 and a rail 534 are provided so that the rods 510 may slide along with the sensor 506 relative to the bracket mount 530 to allow for motion in the, for instance, the anterior-posterior direction.

The sensor system 500 may include only materials that would not interfere with the electromagnetic system of the RKT apparatus or a CT scanner in which the apparatus might be placed during testing. In one example, the sensor system 500 components may include a plastic body or contacting end, brass rods, and stainless steel components. Aluminum could also be used.

With reference to FIG. 10, the sensor system 500 may be initialized (e.g., zeroed out) in an act 345. In knee joint examples, the initialization may establish an unstressed or unbiased position of the patient's femur. In some cases, the sensor system 500 is initialized after the patient's knees are clamped in the act 340. The sensor system 500 may be initialized at other times. For example, initialization may occur after the feet are secured in the act 350, after the tibia positioning assemblies 90 are fixed in the act 360, after the zero-rotation position of the tibias are set about the Z-axis in the act 370, after the length of the tibia rod device 96 is set in the act 380, or v) after the sensors 210 are positioned in the act 390.

The configuration of the joint stabilizer may also vary from the examples shown and described herein. The joint stabilizer frame may not be formed of four or six components and, thus, need not include upper and lower clamping elements 78a, 78b coupled by pairs of guide or adjustment rods 342. Further, the joint stabilizer may aid in more securely retaining the clamped portion of a joint in directions other than the medial/lateral and anterior/posterior directions of the example described above. In one such example, the joint stabilizer may again be a knee stabilizer and may have a clamshell construction with two semi-circular shell sections. Each shell section may carry a portion of a pad, similar to prior examples. The two shell sections may be joined along one edge at a hinge. The opposite edges of the shell sections may be latched to one another and detached from one another to open and close the frame. The hinge(s) and latch(es) may vary considerably in size, shape, form, and function. The shell sections may also vary in shape and size and again may be made from any suitable materials. With the shell closed around a joint, a sensor may be provided on the upper shell section and function as described above to detect residual movement in a joint clamped by the joint stabilizer.

In yet another example, the joint stabilizer may be or include a folding or foldable knee stabilizer or patellar clamp. Such a joint stabilizer may have an upper frame section and a lower frame section connected to one another by two spaced apart side frame sections. In this example, the side frame sections may bend, fold, flex, and/or be hinged to permit movement of the lower frame section relative to the upper frame section. Thus, the joint stabilizer may allow for knee flexion during testing and evaluation. The RKT apparatus may be modified from the aforementioned examples and/or may be otherwise configured to accommodate, for instance, testing of a flexed or bent knee. For example, the side frame sections may be flexible and/or employ one or more hinges to permit movement of the lower frame section relative to the upper frame section during testing.

FIG. 14 depicts a method 1400 of manipulating and evaluating a joint in which residual motion of a stabilized part of the joint is measured for compensation of position data for the joint. The method 1400 may be implemented by any of the examples of the sensor system 500 and joint test apparatus described above. Other test apparatus may be used. The method 1400 may be implemented as part of, or in conjunction with, the methods described above in conjunction with FIGS. 9 and 10. The nature of the joint test may vary. For instance, the method 1400 may be implemented in connection with tests involving different motion characteristics, including anterior-posterior motion, varus-valgus motion, and/or internal-external rotation motion.

The method 1400 may begin in an act 1402 in which a joint is disposed in the test apparatus. The act 1402 may include a number of acts directed to patient and test apparatus setup, including, for instance, applying and/or adjusting one or more stabilizers, such as the thigh stabilizers described above. The setup procedure may include centering the knees or other joints relative to a joint stabilizer, such as the knee stabilizers described above. Additional, alternative, or fewer acts may be implemented. For example, the patient setup procedure and apparatus for stabilizing the femur, thigh, or other bone associated with the joint under test may vary.

In an act 1404, a clamp and/or other joint stabilizer is positioned to stabilize the joint or a portion thereof. In knee test examples, the above-described knee stabilizers may be used to stabilize the knee. For example, the act 1404 may include, correspond with, or otherwise involve the act 340 of the method of FIG. 10, in which a knee stabilizer is clamped down on the knee. In some cases, the act 1404 includes positioning a floating or other sensor carried by the knee stabilizer. For example, the floating sensor of the above-described knee test apparatus may be positioned as described above in connection with the act 345 of the method of FIG. 10. The sensor may be directed to detecting residual motion in one or more directions or degrees of freedom, as described above.

A bracket assembly is applied for residual motion sensing in an act 1406. The application of the bracket assembly may engage opposing sides of the knee or other joint. The bracket assembly is configured to support the detection of residual motion in one or more directions or degrees of freedom, including, for instance, medial-lateral motion. Motion in other direction(s) may be detected, such as other lateral directions. The direction(s) may be other than those detected by the floating sensor. Alternatively or additionally, the bracket assembly is oriented or otherwise applied to detect motion directions or degrees of freedom that may, in other cases, be measured by a floating sensor.

In an act 1408, one or more joint test procedures are implemented. The joint test procedure involves the application of a force (e.g., torque) to the joint to impart motion of a part of the joint, e.g., a tibia, in one or more directions or degrees of freedom. For example, a torque may be directly or indirectly applied to the knee (e.g., the tibia) to drive anterior-posterior motion, varus-valgus motion, and/or internal-external rotational motion of the tibia relative to the femur. The movement direction and other characteristics of the joint test may vary.

Implementing the test(s) in the act 1408 generates data indicative of joint movement. In knee examples, data indicative of the position of the joint may be or include tibial position relative to the femur. Any number of sensors may be used to detect the tibial position. The position data may be directed to measuring joint movement is in one or more directions or degrees of freedom. Data indicative of movement of a clamped portion of the joint (e.g., the femur) in one or more other directions is also generated. Such data may be referred to herein as residual displacement data. The residual displacement data may be generated by one or more sensors, such as the sensor(s) carried by the above-described bracket assembly in connection with the sensor system 500. The sensors may or may not include sensors dedicated or directed to detecting residual motion, such as the sensor(s) carried by the above-described bracket assembly in connection with the sensor system 500.

In an act 1410, the position data for the joint (e.g., the tibia relative to the femur) is adjusted based on the residual displacement data. The residual displacement data may be the data generated via the above-described bracket assembly and sensor(s) directed to detecting residual motion. In knee examples, the residual displacement data generated via the bracket assembly may be indicative of residual motion in the medial-lateral direction. Additional or alternative residual displacement data may be used. For instance, the residual displacement data indicative of residual motion in the anterior-posterior direction may be used to adjust the position data.

The act 1406 may include an act 1412 in which the bracket assembly is adjusted to modify a spacing in which the joint is disposed. The spacing may be between pads or other ends of the bracket assembly. In the knee examples described above, modifying the pad spacing allows ends of the bracket assembly to engage opposing sides of the knee. In some cases, the act 1412 includes disengaging arms and posts of the bracket assembly to allow the length of the arms to be adjusted.

The act 1408 may include a number of steps directed to generating the position data in an act 1414 and generating the residual displacement data in an act 1416. For instance, the steps of the acts 1414, 1416 may involve or include actuating or driving one or more motors while gathering or otherwise obtaining measurements of torque and position, as described above. The acts 1414, 1416 may additionally or alternatively include processing of the raw data collected by the sensors directed to providing such measurements.

The position data may be indicative of, or used to characterize, movement of the joint in one or more degrees of freedom. The direction of the movement may or may not correspond with the direction in which the joint is manipulated. The movement may thus include movement in a primary direction in which the joint is manipulated, as well as movement in one or more secondary directions that result from manipulating the joint in the primary direction.

In some cases, the test procedures of the act 1408 include an AP test and/or a varus-valgus test implemented in an act 1418. In either case, the residual displacement data may be indicative of anterior-posterior movement and/or medial-lateral movement of the clamped portions of the joint (e.g., the femur). The direction associated with the residual displacement data may or may not correspond with the direction in which the joint is manipulated during the test procedure. The test procedures are not limited to the procedures of the act 1418. A variety of different test procedures may be implemented, including, for instance, internal-external rotation test procedure and/or combinations of the above-referenced test procedures.

The direction of the residual motion may vary. For instance, the act 1408 may include the measurement of anterior-posterior residual motion in an act 1420 and/or the measurement of medial-lateral residual motion in an act 1422. Other residual motion directions may also be measured in an act 1424, including, for instance, measurements of the rotation of the clamped portion of the joint (e.g., the femur) in the internal-external direction.

In some cases, the act 1410 includes adjusting position data for a test that manipulates the joint in the same direction as the direction of the residual motion. For example, the position data generated for the tibia during an anterior-posterior translation test may be adjusted in an act 1426 based on the residual displacement data for movement of the knee (e.g., femur) in the anterior-posterior direction. Alternatively or additionally, the position data for the anterior-posterior translation test may be adjusted by other residual displacement data. In still other cases, the residual displacement data for the anterior-posterior direction may be used to adjust the position data generated in other tests in other cases.

Alternatively or additionally, the act 1410 includes adjusting position data for a test that manipulates the joint in a direction different than the direction of the measured residual motion. For example, the position data generated for the tibia during a varus-valgus rotation test may be adjusted in an act 1428 based on the residual displacement data for movement of the knee (e.g., femur) in the medial-lateral direction. Alternatively or additionally, the position data for the varus-valgus test may be adjusted by other residual displacement data. In still other cases, the residual displacement data for the medial-lateral direction may be used to adjust the position data generated in other tests in other cases.

The above-described methods and test apparatus are configured to account and correct for residual motion of a clamped or other portion of a joint otherwise assumed to be stationary during a joint test. In knee examples, the position data for the tibia may be corrected based on residual movement of the knee (e.g., femur). As a result, the disclosed methods and test apparatus aid in reducing error and inconsistency in the test results and the underlying procedures.

The disclosed apparatus allow measurement of residual movement in multiple directions with a single sensor or sensor system. The bracket-based monitoring described herein may be combined with other residual motion monitoring, such as the monitoring provided a floating sensor. Still other residual motion monitoring may be combined with the disclosed monitoring, including, for example, monitoring of rotation of the sensor system, e.g., along the device-based z axis. Monitoring of residual rotation may be useful in connection with internal-external rotation and varus-valgus test procedures. Monitoring of residual rotation may involve a non-slip pad or adhesive disposed on top of the patella such that translation of the patella medially or laterally would register as rotation at the sensor.

The above-described sensor systems are useful in several ways. For example, the system restricts motion to only two dimensions. The restriction minimizes off axis noise. The float assembly and the bracket assembly avoid off-axis noise that would otherwise be generated by other sensors, such as those adhesively stuck to the femur. The introduction of such noise into the position data may cause various problems. The disclosed sensor systems avoid still other problems arising from adhesively attached sensors. For example, such sensors may suffer from poor skin-to-bone interfaces.

The methods described herein may vary from the examples shown. For instance, one or more of the acts may be performed as described but in a different order. Specific steps may be eliminated or altered and additional steps may be added. The design of the RKT apparatus may vary considerably from the example disclosed herein. As the design of the robot or apparatus varies, so may the acts vary, the order of the acts change, the number of acts change, and/or the specific details of the acts be altered or modified. The specific designs of the knee stabilizers and thigh immobilizers may change, whether related to how the devices are assembled, constructed, adjusted, locked, released, or the like. Likewise, the specific designs of the axes drives and/or the overall tibia positioning assemblies may also change.

The systems and methods described above may be used in conjunction with a manual method of testing and/or determining the clamping or engagement force of a joint stabilizer on a knee joint. In one example, the joint stabilizer may include a simple hanging weight, spring, or screw mechanism that may indicate the applied joint stabilizer force. A simple meter or force sensor may be used to measure and determine such force. Alternatively, the joint stabilizer and/or RKT apparatus may be modified to more consistently and/or automatically determine the joint clamping force being applied to the knee joint of a patient. In one example, one or more pressure sensors may be provided on or within the pads of the joint stabilizer. The sensors may automatically determine the joint clamping force. The sensors may also be coupled to a processor, computer, or the like to provide pressure data automatically. The data may be stored, may be utilized in any force and movement calculations, evaluations, and/or diagnoses, and/or may be visibly displayed as needed.

The present disclosure has been described with reference to specific examples that are intended to be illustrative only and not to be limiting of the disclosure. Changes, additions and/or deletions may be made to the examples without departing from the spirit and scope of the disclosure.

The foregoing description is given for clearness of understanding only, and no unnecessary limitations should be understood therefrom.

What is claimed is:

1. An apparatus for manipulation and evaluation of a joint, the apparatus comprising:
    a frame to support the joint;
    a drive supported by the frame, the drive being configured to manipulate, in a first direction, a bone connected to the joint during the evaluation of the joint;
    a clamp supported by the frame, the clamp being configured to stabilize a part of the joint during the evaluation of the joint;
    a bracket assembly carried by the clamp, the bracket assembly being configured to engage the joint, the bracket assembly being moveable relative to the clamp in a second direction different than the first direction; and
    a sensor coupled to the bracket assembly such that the sensor is moved by displacement of the bracket assembly relative to the clamp in the second direction during the evaluation of the joint, the sensor being configured to generate a signal indicative of the displacement;
    wherein the displacement is indicative of movement of the part of the joint stabilized by the clamp, the movement being in the second direction.

2. The apparatus of claim 1, wherein respective ends of the bracket assembly engage medial and lateral sides of the joint.

3. The apparatus of claim 1, wherein the displacement comprises medial-lateral translation.

4. The apparatus of claim 1, wherein:
    the joint includes a first bone and a second bone;
    the first bone is the bone manipulated by the drive;
    the clamp is configured to stabilize the second bone; and
    the displacement is indicative of residual movement of the second bone during the joint evaluation.

5. The apparatus of claim 4, further comprising a processor configured to adjust position data for the first bone in accordance with data indicative of the displacement to compensate for the residual movement of the stabilized part of the joint during the joint evaluation.

6. The apparatus of claim 1, further comprising a linear bearing mounted on the frame, wherein:
   the bracket assembly comprises a bar disposed in the linear bearing; and
   the sensor is mounted on the bar such that the displacement includes translation of the bar within the linear bearing.

7. The apparatus of claim 6, further comprising a rod attached to the sensor, wherein:
   the rod extends from the sensor to establish a contact point with the joint; and
   the sensor is slidably coupled to the bar to allow displacement of the rod and the sensor as a result of movement of the joint in a direction other than a direction of the translation.

8. The apparatus of claim 6, wherein the bracket assembly comprises:
   a pair of link posts extending from the bar to position respective ends of the bracket assembly along opposite sides of the joint;
   a pair of arms, each arm of the pair of arms extending laterally inward from a respective link post of the pair of link posts toward a respective side of the opposite sides of the joint; and
   a pair of pads, each pad of the pair of pads disposed on a respective side of the opposite sides of the joint.

9. The apparatus of claim 8, wherein connections between the pair of arms and the pair of link posts are adjustable to modify a spacing between the pair of pads.

10. The apparatus of claim 6, wherein the translation of the bar is indicative of the movement of the part of the joint stabilized by the clamp.

11. The apparatus of claim 6, wherein the translation of the bar is in the second direction.

12. The apparatus of claim 1, wherein the bracket assembly comprises a pair of link posts configured to position respective ends of the bracket assembly along opposite sides of the joint such that the pair of link posts and the respective ends are moved in the second direction during the displacement of the bracket assembly.

13. The apparatus of claim 1, wherein the bracket assembly comprises a pair of arms extending laterally inward toward opposite sides of the joint such that the pair of arms are moved in the second direction during the displacement of the bracket assembly.

14. The apparatus of claim 1, wherein the bracket assembly comprises a pair of pads disposed on opposite sides of the joint such that the pair of pads are moved in the second direction during the displacement of the bracket assembly.

* * * * *